(12) United States Patent
de Boer et al.

(10) Patent No.: US 6,315,998 B1
(45) Date of Patent: *Nov. 13, 2001

(54) METHODS OF BLOCKING B-CELL ACTIVATION USING ANTI-CD40 MONOCLONAL ANTIBODIES

(75) Inventors: Mark de Boer, Beuerwijk (NL); Leah B. Conroy, Pacifica, CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/504,505

(22) Filed: Feb. 15, 2000

Related U.S. Application Data

(60) Continuation of application No. 08/463,893, filed on Jun. 5, 1995, now Pat. No. 6,056,955, which is a division of application No. 08/070,158, filed on May 28, 1993, now Pat. No. 5,677,165, which is a continuation-in-part of application No. 07/910,222, filed on Jul. 9, 1992, now Pat. No. 5,397,703.

(51) Int. Cl.$^7$ .................... A61K 39/395; C07K 16/28
(52) U.S. Cl. ................... 424/144.1; 424/130.1; 424/133.1; 424/141.1; 424/143.1; 424/153.1; 424/173.1; 530/387.1; 530/387.3; 530/388.1; 530/388.2; 530/388.22; 530/388.7; 530/388.73
(58) Field of Search ............. 424/130.1, 143.1, 424/173.1; 530/387.1, 388.2, 388.73

(56) References Cited

U.S. PATENT DOCUMENTS

| | | |
|---|---|---|
| 4,355,023 | 10/1982 | Ehrlich et al. . |
| 4,689,299 | 8/1987 | Insel et al. . |
| 4,886,796 | 12/1989 | Eichner et al. . |
| 4,923,872 | 5/1990 | Kostlan et al. . |
| 5,068,223 | 11/1991 | Lipsky et al. . |
| 5,100,899 | 3/1992 | Calne . |
| 5,182,368 | 1/1993 | Ledbetter et al. . |
| 5,677,165 | 10/1997 | de Boer et al. . |
| 5,874,082 | 2/1999 | de Boer et al. . |
| 6,004,552 | * 12/1999 | De Boer et al. . |

FOREIGN PATENT DOCUMENTS

| | | |
|---|---|---|
| 0 434 879 A1 | 7/1991 | (EP) . |
| 0 555 880 A2 | 8/1993 | (EP) . |
| WO 90/07861 | 7/1990 | (WO) . |
| WO 92/00092 | 1/1992 | (WO) . |
| WO 94/04570 | 3/1992 | (WO) . |
| WO 93/08207 | 4/1993 | (WO) . |
| WO 93/11794 | 6/1993 | (WO) . |
| WO 94/01457 | 1/1994 | (WO) . |
| WO 94/01547 | 1/1994 | (WO) . |
| WO 95/09653 | 4/1995 | (WO) . |

OTHER PUBLICATIONS

Armitage, et al., *Molecular and Biological Characterization of a Murine Ligand for CD40*, Nature 357:80–82 (May 7, 1992).

Banchereau, et al. Long–Term Human B Cell Lines Dependent on Interleukin–4 and Antibody to CD40, Science 251:70–72 (Jan. 4, 1991).

Banchereau, et al., Growing Human B Lymphocytes in the CD40 System, Nature 353:678–679 (Oct. 17, 1991).

Chothia, et al., Canonical Structures for the Hypervariable Regions of Immunoglobulins, J. Mol. Biol. 196:901–917 (1987).

Claassen, et al., Mononuclear cells from patients with the hyper–IgE syndrome produce with IgE when they are stimulated with recombinant human interleukin–4, J. Allergy Clin., Immunol. 88:713–721 (1994).

Clark, et al., Activation of Human B Cells Mediated Through Two Distinct Cell Surface Differentiation Antigens, Bp35 and Bp50, Proc. Natl. Acad. Sci. USA 83:4494–4498 (Jun. 1986).

Clark, et al., Association Between IL–6 and CD40 Signaling IL0–6 Induces Phosphorylation of CD40 Receptors, J. Immunol. 145(5):1400–1406 (Sep. 1, 1990).

Cosimi, et al., Use of Monoclonal Antibodies to T–Cell Subsets for Immunologic Monitoring and Treatment in Recipients of Renal Allografts, N. Eng. J. Med. 305(6):308–313 (Aug. 6, 1981).

de Boer, et al., Generation of Monoclonal Antibodies to Human Lymphocyte Cell Surface Antigens Using Insect Cells Expressing Recombinant Proteins, J. Immunol., Meth. 152:15–23 (1992).

DeFranco, et al., Separate Control of B Lymphocyte Early Activation and Proliferation in Response to Anti–IgM Antibodies, The Journal of Immunology 135(1)87–94 (Jul. 1985).

DiSanto, et al., Generation of anti–human CD8β–specific antibodies using transfectants expressing mixed–species CD8 heterodimers, J. Immunol. Methods 141:123–131 (1991).

(List continued on next page.)

*Primary Examiner*—Phillip Gambel
(74) *Attorney, Agent, or Firm*—Donald J. Pochopien; Lisa E. Alexander; Robert P. Blackburn

(57) ABSTRACT

Methods for preventing or treating an antibody-mediated diease in a patient are presented, the methods comprising administration of a monoclonal antibody capable of binding to a human CD40 antigen located on the surface of a human B cell, wherein the binding of the antibody to the CD40 antigen prevents the growth or differentiation of the B cell. Monoclonal antibodies useful in these methods, and epitopes immunoreactive with such monoclonal antibodies are also presented.

20 Claims, 12 Drawing Sheets

OTHER PUBLICATIONS

Edgington, How Sweet it is: Selectin–Mediating Drugs, Biotechnology 10:383–389 (1992).

Fanslow, et al., CD40 Mabs M2 and M3 inhibit CD40L Binding and Function, Tissue Antigens 42(3):304 (Oct. 1993).

Francisco, et al., Activity of a Single–Chain Immunotoxin that Selectively Kills Lymphoma and Other B–Lineage Cells Expressing the CD40 Antigen, Cancer Research 55:3099–3104 (Jul. 15, 1995).

Freedman, et al., B7, A B Cell–Restricted Antigen that Identifies Preactivated B Cells, The Journal of Immunology 139(10):3260–3267 (Nov. 15, 1997).

Garrone, et al., mAb 104, a new monoclonal antibody, recognizes the B7 antigen that is expressed on activated B cells and HTLV–1 transformed T cells, Immunology 69:531–535 (1990).

Gascan, et al., Anti–CD40 Monoclonal Antibodies or CD4$^+$ T Cell Clones andIL–4 Induce IgG4 and IgE Switching in Purified Human B Cells Vai Different Signaling Pathways, The Journal of Immunology 147(1):8–13 (Jul. 1, 1991).

Gauchat, et al., Modulation of Il–4 induced germline εRNA synthesis in human B cells by tumor necrosis factor–α, anto–CD40 monoclonal antibodies of transforming growth factor–β correlates with levels of IgE production, International Immunology 4(3):397–406 (1991).

Golub, Immunology a Synthesis, Sinauer Assoc. Inc., Sunderland, MA. pp. 19–20 (1987).

Gordon, et al., Resting B Lymphocytes can be Triggered Directly Through the CDw40 (Bp50) Antigen, A Comparison with Il–4–Mediated Signaling, The Journal of Immunology 140(5):1425–1430 (Mar. 1, 1988).

Gray, et al., Memory B Cell Development butnot Germinal Center Formation is Impaired by In Vivo Blockade of CD40–CD40 Ligand Interaction, J. Exp. Med. 180:141–155 (Jul. 1994).

Gruber, et al., Anti–CD45 Inhibition of Human B Cell Proliferation Depends on the Nature of Activation Signals and the State of B Cell Activation, J. Immunol. 142(12):4144–4152 (Jun. 15, 1989).

Harris, et al., Therapeutic antibodies–the coming of age, Tibtech 11:42–44 (Feb. 1993).

Hartog, et al., Generation of a humanized anti–CD40 mab for treatment of autoimmune diseases. Immunotechnology 2(4):299 (Nov. 1996) (abstract).

Jabara, et al., CD40 and IgE: Synergism between Anti–CD40 Monoclonal Antibody and Interleukin 4 in the Induction of IgE Synthesis by Highly Purified Human B Cells, J. Exp. Med. 172:1861–1864 (Dec. 1990).

June, et al., Role of the CD28 Receptor in T–cell activation, Immunology Today 11(6):211–216 (1990).

Jung, et al., Selective Inhibition of Growth Factor–Dependent Human B Cell Proliferation by Monoclonal Antibody AB1 to an Antigen Expressed by Activated B Cells, J. Exp. Med 160:1919–1924 (Dec. 1984).

Kabat, et al., Sequences of Proteins of Immunological Interest, Tabulation and Analysis of Amino Acid and Nucleic Acid Sequences of Precursors, V–Regions, C0–Regions, J–Chain, $\beta_2$–Microglobulins, Major Histocompatibility Antigens, Thy–1, Complement, c–Reactive Protein, Thymopoietin, Post–gamma Globulin, and $\alpha_2$–Macroglobulin, sponsored through Contract NO1–RR–8–2118 by components of the National Institutes of Health, Bethesda, MD 20205 (1983).

Kahan, Immunosuprressive therapy, Curr. Opin Immunology 4:553–560 (1992).

Knight, et al., The Immunogenicity of the 7E3 Murine Monoclonal FAB Antibody Fragment Variable Region is Dramatically Reduced in Humans by Substitution of Human for Murine constant Regions, Molecular Immunology 32(16):1271–1281 (1995).

Kriegler, et al., A Novel Form of TNF/Cachectin is a Cell Surface Cytotoxic Transmembrane Protein:Ramifications for the Complex Physiology of TNF, Cell 53:45–53 (1988).

Kwekkeboom, et al., CD40 plays an essential role in the activation of human B Cells by Murine EL485 cells, Immunology 79:439–444 (1993).

Lane, et al., Activated human T cells express a ligand for the human B Cell–associated antigen CD40 which participates in T cell–dependent activation of B lymphocytes, Eur. J. Immunol 22:2573–2578 (1992).

Ledman, et al., Anti–CD40 Monoclonal Antibody Blocks the Contract Dependent T Helper Signal Mediated by 5C8 Ag., Clinical Research 40:154A (1992).

Linsley, et al., CTLA–4 is a Second Receptor for the B Cell Activation Antigen B7, J. Exp. Med. 174:561–569 (Sep. 1991).

Muraguchi, et al., Sequential Requirements for Cell Cycle Progression of Resting Human B Cells after Activation by Anti–Ig, The Journal of Immunology 132(1):176–180 (1984).

Noelle, et al., T Helper Cells, Current Opinion in Immunology 4:333–337 (1992).

Padlan, et al., A Possible Procedure for Reducing the Immunogenicity of Antibody Variable Domains While Preserving Their Ligan–Binding Properties, Molecular Immunology 28(4/5):489–498 (1991).

Paul (ED) Fundamental Immunology Raven Press NY 1993 Chapter 8: Immunogenicity and Antigen Structure p. 242 only.

Paulie, et al., The Human B Lymphocyte and Carcinoma Antigen, CDw40, is a Phosphoprotein Involved in Growth Signal Transduction, J. Immunol. 142(2):590–595 (Jan. 15, 1989).

PCT Written Opinion, International Application No. PCT/US97/02858 dated Jun. 23, 1997.

PCT Written Opinion, International Application No. PCT/US97/02958 dated Nov. 21, 1997.

Ross, et al., Characterization of nerve growth factor receptor in neural crest tumors using monoclonal antibodies, Proc. Natl. Acad. Sci. USA 81:6681–6685 (Nov. 1984).

Rousset, et al., Cytokine–induced Proliferation and Immunoglobulin Production of Human B Lymphocytes Triggered through Their CD40 Antigen, J. Exp. Med. 173:705–710 (Mar. 1991).

Sato, et al., Biological Effects in Vitro of Monoclonal Antibodies to Human Epidermal Growth Factor Receptors, Mol. Biol. Med. 1:511–529 (1983).

Splawski, et al., Immunoregulatory Role of CD40 In Human B Cell Differentiation, The Journal of Immunology 150:1276–1285 (Feb. 15, 1993).

Stamenkovic et al., A B–lymphocyte Activation Molecule Related to the Nerve Growth Factor Receptor and Induced by Cytokines in Carcinomas, EMBO Journal 8(5):1403–1410 (1989).

Stuber, et al., Blocking the CD40L–CD40 Interaction in vivo specifically prevents the priming of T Helper 1 Cells through the inhibition of Interleukin 12 Secretion, J. Exp. Med. 183:693–698 (1996).

Tanaka, et al., Distinct Reactivities of four Monoclonal Antibodies with Human Interleukin 2 Receptor, Microbial. Immunol. 29(10):959–972 (1985).

Uckun, et al., Temporal Association of CD40 Antigen Expression with Discrete Stages of Human B–Cell Ontogeny and the Efficacy of Anti–CD40 Immunotoxins Against Clonogenic B–Lineage Acute Lymphoblastic Leukemia as Well as B–Lineage Non–Hodgin's Lymphoma Cells, Blood 76(12):2449–2456 (Dec. 15, 1990).

Valle, et al., mAb, 104, A New Monoclonal Antibody, Recognized the B7 Antigen that is Expressed on Activated B Cells HTLV–1–Transformed T Cells, Immunology, 69:531–535 (1990).

Ward, et al., Blocking of adhesion molecules in vivo as anti–inflammatory therapy, Therapeutic Immunology 1:165–171 (1994).

Webb, et al., Cell–Surface Expression and Purification of Human CD4 Produced in Baculovirus–Infected Insect Cells, Proc. Natl. Acad. Sci. USA 86:7731–7735 (Oct. 1989).

Wetzel, et al., Evidence for Two Distinct Activation States Available to B Lymphocytes, The Journal of Immunology 133(5):2327–2332 (Nov. 1984).

Winter, et al., Antibody–based Therapy, Humanized Antibodies, TIPS 14:139–143 (1993).

Yellin, et al., CD40 Molecules Induce Down–Modulation and Endocytosis of T Cell Surface T Cell–B Cell Activating Molecule/CD40–L, J. of Immunology 152:598–608 (1994).

Zhang, et al., CD40 Stimulation Provides an IFN–γ–Independent and IL–4 Dependent Differentiation Signal Directly to Human B Cells for IgE Production, Journal of Immunology 146(6):1836–1842 (Mar. 15, 1991).

Boussiotis, et al., Activated Human B Lymphocytes Express Three CTLA–4 Counterreceptors That Costimulate T–Cell Activation, Proc. Natl. Acad. Sci. USA 90:11059–11063 (Dec. 1993).

de Boer, et al., Functional Characterization of a Novel Anti–B7 Monoclonal Antibody, Eur. J. Immunology 22 (12):3071–3075 (Dec. 1992).

Freeman, et al., B7, A New Member of the Ig Superfamily with Unique Expression on Activated and Neoplastic B Cells, The Journal of Immunology, 143(8):2714–2722 (Oct. 1989).

Freeman, et al., Cloning of B7–2: A CTLA–4 Counter-Receptor That Costimulates Human T Cell Proliferation, Science 262:909–911 (1993).

Jenkins, et al., Antigen Presentation by chemically Modified Splenocytes Induces Antigen–Specific T Cell Unresponsiveness in Vitro and in Vivo, Journal of Experimental Medicine 165:302–319 (Feb. 1987).

Jenkins, et al., Molecular Events in the Induction of a Nonresponsive State in Interleukin 2–Producing Helper T–Lymphocyte Clones, Proc. Natl. Acad. Sci. USA 84:5409–5413 (Aug. 1987).

Vandenberghe et al., In situ Expression of B7/BB1 On Antigen–Presenting cells and activated B Cells: and Immunohistochemical Study, International Immunology 5(3):317–321 (Mar. 1993).

* cited by examiner

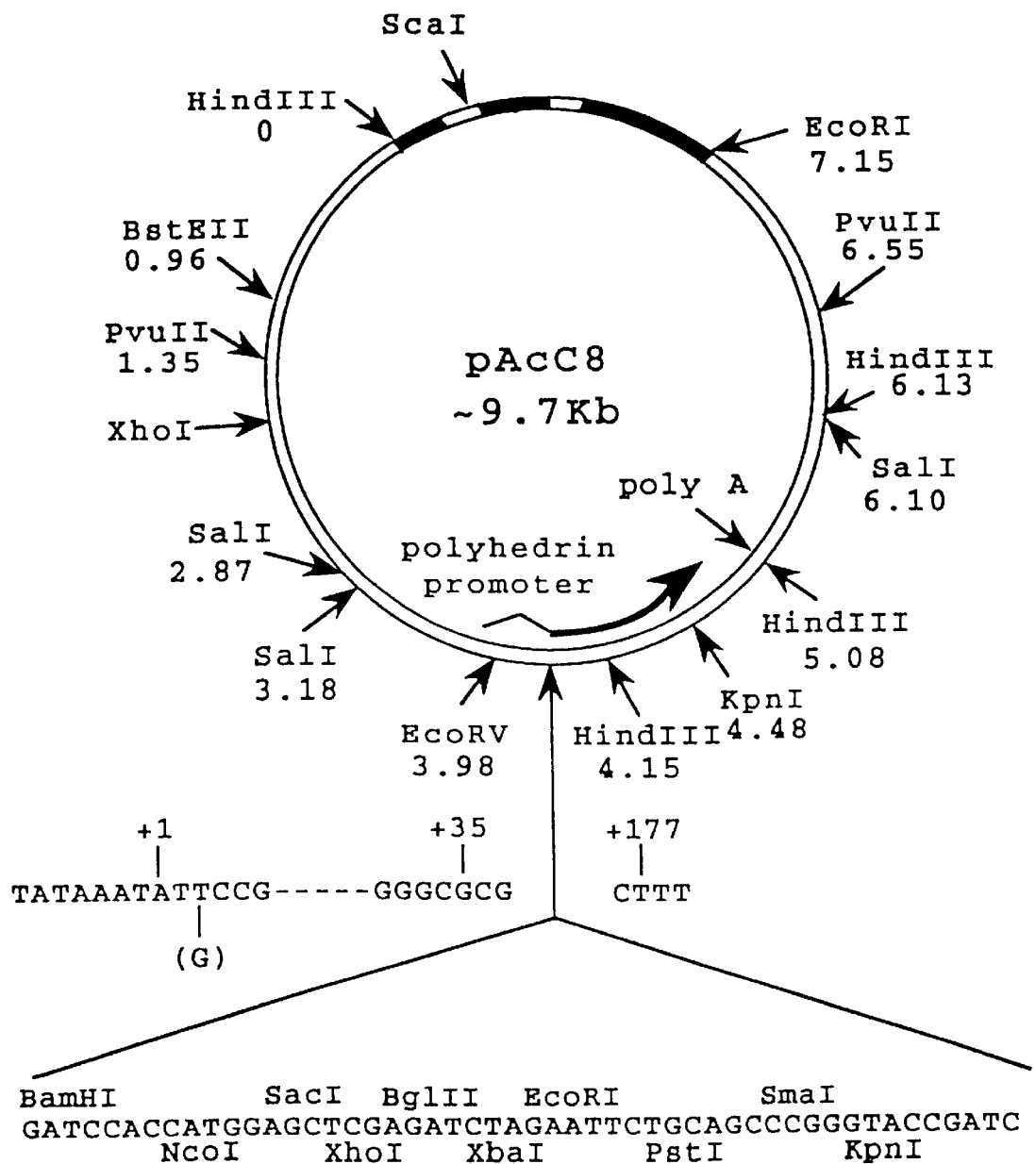
FIG. IA

Full length B7:

Forward  MR67  5'-GCG CTGCAG CATCTGAAGCCATGGGCC-3'  (307-324)

Backward MR68  5'-CGC GGTACC TTGCTTCTGCGGACACTG-3'  (1182-1199)

Soluble B7:

Forward  MR67  5'-GCG CTGCAG CATCTGAAGCCATGGGCC-3'  (307-324)

Backward MR145 5'-GCGC GGTACC TTACTCCATGGGCATGTATTCCTCTCTTCCTCGTTATCAGGAAAATGCTGTTG-3'  (1022-1042)

Full length CD40:

Forward  MR108 5'-GCGT AGATCT GGTCTCACCTGGCCATGGTTCG-3'  (34-55)

Backward MR112 5'-GCGT GGTACC CCACACTCCTGGGTGGGTGCAGCC-3'  (882-905)

Soluble CD40:

Forward  MR108 5'-GCGT AGATCT GGTCTCACCTGGCCATGGTTCG-3'  (34-55)

Backward MR150 5'-GCGT GGTACC TTACTCCATGGGCATGTATTCCTCTTCCTCATCAGTCTTGTTGTGCCTGC-3'  (575-596)

FIG. 2

METHODS OF BLOCKING B-CELL ACTIVATION USING ANTI-CD40 MONOCLONAL ANTIBODIES

CROSS-REFERENCE TO RELATED APPLICATIONS

This application is a continuation of U.S. Ser. No. 08/463,893, filed Jun. 5, 1995, now U.S. Pat. No. 6,056,959, which is a divisional application of U.S. Ser. No. 08/070,158, filed May. 28, 1993, now U.S. Pat. No. 5,677,165, which is a continuation-in-part of U.S. Ser. No. 07/910,222, filed Jul. 9, 1992, now U.S. Pat. No. 5,397,703, currently pending, the disclosure of which is hereby incorporated by reference.

FIELD OF THE INVENTION

This invention relates to novel methods of treating diseases of the immune system. In particular, this invention relates to methods of preventing or treating antibody-mediated diseases such as IgE-mediated disease (allergies) and autoimmune diseases including sytemic lupus erythematosus (SLE), primary biliary cirrhosis (PBC), and idiopathic thrombocytopenic purpura (ITP).

BACKGROUND OF THE INVENTION

I. B-Cell Activation

B cells play an important role during the normal in vivo immune response. A foreign antigen will bind to surface immunoglobulins on specific B cells, triggering a chain of events including endocytosis, processing, presentation of processed peptides on MHC-class II molecules, and up-regulation of the B7 antigen on the B-cell surface. A specific T cell then binds to the B cell via T-cell receptor (TCR) recognition of processed antigen presented on the MHC-class II molecule. Stimulation through the TCR begins to activate the T cell and initiates T-cell cytokine production. Interaction between the CD28 antigen on T cells and the B7 antigen on B cells can provide a second signal further activating the T cell, resulting in high level cytokine secretion. Additionally, the CD40 ligand, which is not expressed on resting human T cells, is up-regulated on the T-cell surface when the above-mentioned signals are received. The B cell is then stimulated by the CD40 ligand through the CD40 antigen on the B-cell surface, and also by soluble cytokines, causing the B cell to mature into a plasma cell secreting high levels of soluble immunoglobulin.

II. The EL4B5 Cell Line

A few years ago, Zubler et al., *J. Immunol.* (1985) 134:3662, observed that a mutant subclone of the mouse thymoma EL-4 line, known as EL4B5, could strongly stimulate B cells of both murine and human origin to proliferate and differentiate into immunoglobulin-secreting plasma cells in vitro. This activation was found to be antigen-independent and not MHC restricted. For optimal stimulation of human B cells, the presence of supernatant from activated human T cells was needed, but a B-cell response also occurred when EL4B5 cells were preactivated with phorbol-12-myristate 13-acetate (PMA) or IL-1. Zubler et al., *Immunological Reviews* (1987) 99:281; and Zhang et al., *J. Immunol.* (1990) 144:2955. B-cell activation in this culture system is efficient—limiting dilution experiments have shown that the majority of human B cells can be activated to proliferate and differentiate into antibody-secreting cells. Wen et al. *Eur. J. Immunol.* (1987) 17:887.

The mechanism by which these mutant EL-4 cells activate both murine and human B cells has not been elucidated previously. It is, however, clear that cell-cell contact is required for EL4B5-induced B-cell activation. First, B cells do not proliferate in the presence of supernatant from PMA-stimulated EL4B5 cells. Zubler et al. (1985) supra. Second, B cells do not proliferate when they are separated from PMA-tated EL4B5 cells by a semipermeable filter membrane. Zhang et al., supra. Antibodies against mouse LFA-1, human LFA-1 or human LFA-3 and antibodies against mouse or human MHC class II molecules do not inhibit EL4B5-induced proliferation of human or murine B cells. Zubler et al. (1987) and Zhang et al., supra.

III. The CD40 Antigen the CD40 Antigen Ligand, and Anti-CD40 Antibodies

The CD40 antigen is a glycoprotein expressed on the cell surface of B cells. During B-cell differentation the molecule is first expressed on pre-B cells and then disappears from the cell surface when the B cell becomes a plasma cell. Crosslinking of the CD40 molecules with anti-CD40 antibodies mediates a variety of effects on B cells. The CD40 antigen is known to be related to the human nerve growth factor (NGF) receptor and tumor necrosis factor-alpha (TNF-α) receptor, suggesting that CD40 is a receptor for a ligand with important functions in B-cell activation.

A ligand for CD40 has been identified on the cell surface of activated T cells. Fenslow et al., *J. Immunol.* (1992) 149:655; Lane et al., *Eur. J. Immunol.* (1992) 22:2573; Noelle et al., *Proc. Natl. Acad. Sci.* (*USA*) (1992) 89:6550. cDNA cloning of the CD40 ligand revealed a molecule with characteristics of a type-II transmembrane glycoprotein with homology to TNF-α. Armitage et al., *Nature* (1992) 357:80 and Spriggs et al., *J. Exp. Med.* (1992) 176:1543. The extracellular domain of the CD40 ligand contains two arginine residues proximal to the transmembrane region, providing a potential proteolytic cleavage site that could give rise to a soluble form of the ligand. Expression of recombinant CD40 ligand has demonstrated that this molecule can stimulate the proliferation of purified B cells and, in combination with IL-4, mediate the secretion of IgE. Armitage et al. and Spriggs et al., supra. It has been reported that abnormalities in the gene for the CD40 ligand, resulting in the absence of a functional molecule on activated T cells, is responsible for the occurrence of X-linked hyper-IgM syndrome, a rare disorder characterized by the inability of these patients to produce normal levels of antibody isotypes other than IgM. Allen et al., *Science* (1993) 259:990; and Korthäuer et al., *Nature* (1993) 361:539.

All anti-CD40 antibodies known in the art have a stimulatory effect on human B cells. Cross-linking of the CD40 molecule on the B-cell surface using known anti-CD40 antibodies mediates a variety of effects on B cells. Anti-CD40 monoclonal antibodies (mAbs) can induce intercellular adhesion, proliferation and, in combination with certain cytokines, maturation to antibody secreting cells. For example, known anti-CD40 mAbs have been shown to mimic the effects of T helper cells in B-cell activation. When presented on adherent cells expressing FcγRII, these antibodies induce Bell proliferation. J. Banchereau et al., *Science* (1989) 251:70. Moreover, the known anti-CD40 mAbs can replace the T helper signal for secretion of IgM, IgG and IgE in the presence of IL-4. H. Gascan et al., *J. Immunol.* (1991) 147:8. Furthermore, known anti-CD40 mAbs can prevent programmed cell death (apoptosis) of B cells isolated from lymph nodes.

However, the anti-CD40 antibodies known in the art stimulate B cells but are incapable of inhibiting the B-cell response. Furthermore, no anti-CD40 antibodies are known that are (1) capable of inhibiting the B-cell response and (2) can be used to prevent or treat antibody-mediated disease.

SUMMARY OF THE INVENTION

The current invention is based on the discovery of anti-CD40 antibodies that do not stimulate the growth and differentiation of human B cells. In contrast, these antibodies can inhibit human B-cell responses at relatively low concentrations. Accordingly, these antibodies can be used to prevent or treat diseases or conditions that are mediated by antibodies produced by the human B-cell response. These antibodies also recognize novel epitopes on the CD40 antigen useful in modulating the B-cell response.

Accordingly, it is a primary object of this invention to provide a monoclonal antibody capable of binding to a human CD40 antigen located on the surface of a human B cell, wherein the binding of the antibody to the CD40 antigen prevents the growth or differentiation of the B cell.

It is a further object of this invention to provide a method for preventing or treating an antibody-mediate disease in a patient, the method comprising administering to a patient in need of such treatment a therapeutically effective amount of a monoclonal antibody capable of binding to a human CD40 antigen located on the surface of a human B cell, wherein the binding of the antibody to the CD40 antigen prevents the growth or differentiation of the B cell, in a pharmaceutically acceptable excipient.

It is another object of this invention to provide a method for preventing or treating an IgE-mediated disease such as an allergy in a patient, the method comprising administering to a patient in need of such treatment a therapeutically effective amount of a monoclonal antibody capable of binding to a human CD40 antigen located on the surface of a human B cell, wherein the binding of the antibody to the CD40 antigen prevents the growth or differentiation of the B cell, in a pharmaceutically acceptable excipient.

It is yet another object of this invention to provide a method for preventing or treating an antibody-mediated autoimmune disease in a patient, the method comprising administering to a patient in need of such treatment a therapeutically effective amount of a monoclonal antibody capable of binding to a human CD40 antigen located on the surface of a human B cell, wherein the binding of the antibody to the CD40 antigen prevents the growth or differentiation of the B cell, in a pharmaceutically acceptable excipient. Particular autoimmune diseases contemplated for treatment by this method include sytematic lupus erythematosus (SLE), primary biliary cirrhosis (PBC), and idiopathic thrombocytopenic purpura (ITP).

It is a further object of this invention to provide a CD40 antigen epitope capable of competing with the binding of a CD40 antigen to an anti-CD40 monoclonal antibody wherein the binding of that antibody to a human CD40 antigen located on the surface of a human B cell prevents the growth or differentiation of the B cell.

In more preferred embodiments of the above objects, the monoclonal antibody is either 5D12, 3A8 or 3C6.

BRIEF DESCRIPTION OF THE DRAWINGS

FIG. 1A shows a schematic representation of the baculoviral transfer vector pAcC8 and the sequence of the multiple cloning site (SEQ ID NO: 1). As shown, the multiple cloning site was inserted between nucleotide number +37 and +176 of the polyhedrin gene.

FIG. 2 shows the sequences of polymerase chain reaction primers used in the preparation of coding regions for human CD40 and human B7 antigens. These primers were constructed on the basis of the published complete DNA coding sequences for antigens B7 and CD40. Specifically shown are the primers for full length B7, which are designated as MR67 (SEQ ID NO: 2) and MR69 (SEQ ID NO: 3); the primers for soluble B7, which are designated as MR67 (SEQ ID NO: 2) and MR145 (SEQ ID NO: 4); the primers for full length CD40, which are designated as MR108 (SEQ ID NO: 5) and MR112 (SEQ ID NO: 6); and the primers for soluble CD40, which are designated as MR108 (SEQ ID NO: 5) and MR150 (SEQ ID NO: 7).

FIG. 4A shows the results of staining ARC EBV transformed cells with serum from a mouse immunized with B7 expressing Sf9 cells (solid line) or with normal mouse serum (dotted line). FIG. 4B shows the results of staining ARC EBV transformed cells with serum from a mouse immunized with CD40 expressing Sf9 cells (solid line) or with normal mouse serum (dotted line). FIG. 4C shows the results of staining ARC EBV transformed cells with serum from a mouse imunized with control Sf9 cells (solid line) or with normal mouse serum (dotted line).

DETAILED DESCRIPTION OF THE INVENTION

Figure 1B:
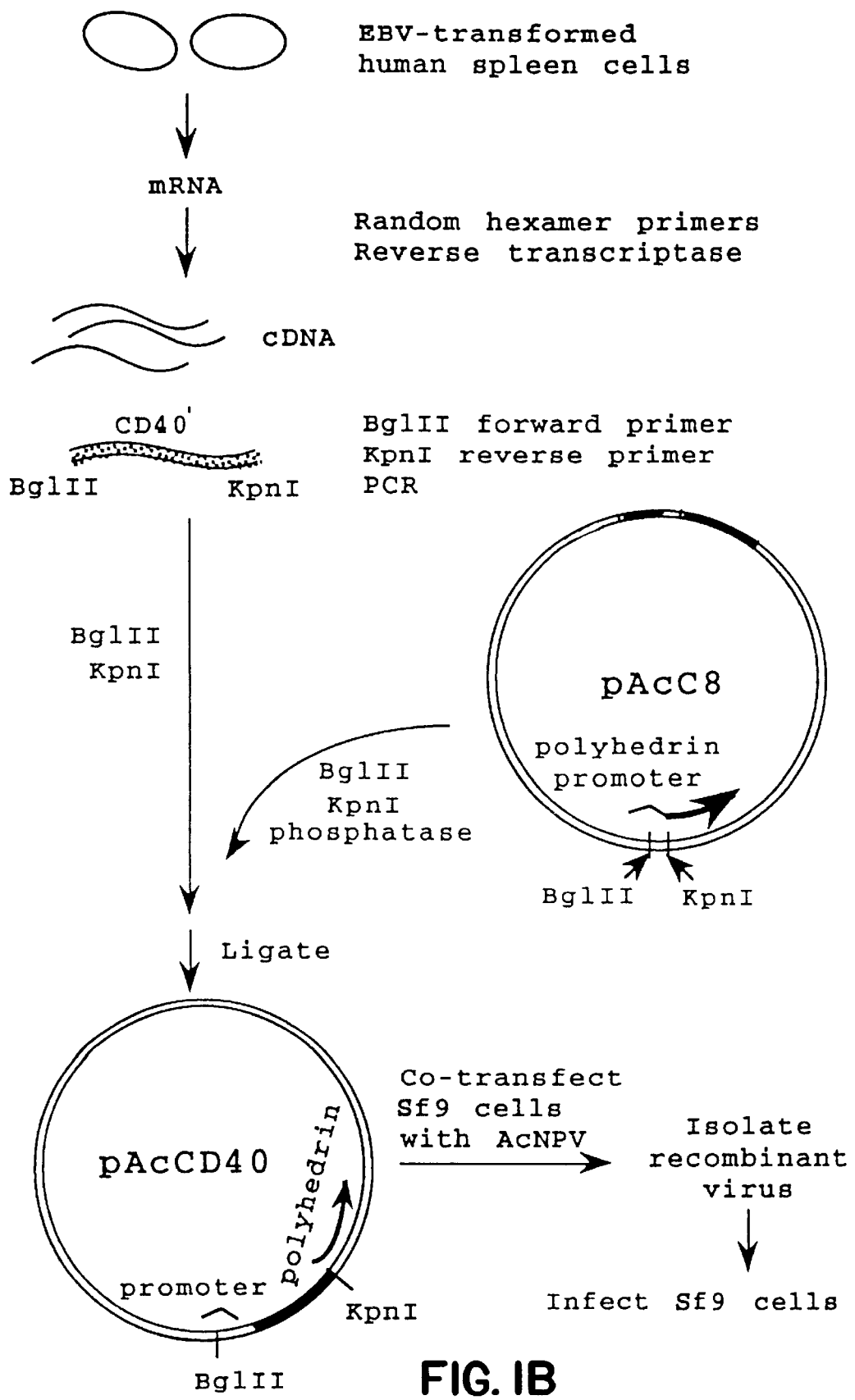
FIG. 1B shows a schematic representation of the generation of Sf9 cells which express human CD40 or B7 antigen.

The invention described herein draws on previously published work and pending patent applications. By way of example, such work consists of scientific papers, patents or pending patent applications. All of these publications and applications, cited previously or below are hereby incorporated by reference.

Definitions

As used herein, the term "antibody" refers to polyclonal antibodies, monoclonal antibodies, humanized antibodies, single-chain antibodies, and fragments thereof such as $F_{ab}$, $F_{(ab')2}$, $F_v$, and other fragments which retain the antigen binding function of the parent antibody.

As used herein, the term "monoclonal antibody" refers to an antibody composition having a homogeneous antibody population. The term is not limited regarding the species or source of the antibody, nor is it intended to be limited by the manner in which it is made. The term encompasses whole immunoglobulins as well as fragments such as $F_{ab}$, $F_{(ab')2}$, $F_v$, and others which retain the antigen binding function of the antibody. Monoclonal antibodies of any mammalian species can be used in this invention. In practice, however, the antibodies will typically be of rat or murine origin because of the availability of rat or murine cell lines for use in making the required hybrid cell lines or hybridomas to produce monoclonal antibodies.

As used herein, the term "humanized antibodies" means that at least a portion of the framework regions of an immunoglobulin are derived from human immunoglobulin sequences.

As used herein, the term "single chain antibodies" refer to antibodies prepared by determining the binding domains (both heavy and light chains) of a binding antibody, and supplying a linking moiety which permits preservation of the binding function. This forms, in essence, a radically abbreviated antibody, having only that part of the variable domain necessary for binding to the antigen. Determination and construction of single chain antibodies are described in U.S. Pat. No. 4,946,778 to Ladner et al.

The term "CD40 antigen epitope" as used herein refers to a molecule which is capable of immunoreactivity with the anti-CD40 monoclonal antibodies of this invention, excluding the CD40 antigen itself. CD40 antigen epitopes may comprise proteins, protein fragments, peptides, carbohydrates, lipids, and other molecules, but for the purposes of the present invention are most commonly proteins, short oligopeptides, oligopeptide mimics (i.e., organic compounds which mimic the antibody binding properties of the CD40 antigen), or combinations thereof. Suitable oligopeptide mimics are described, inter alia, in PCT application US91/04282.

The Antibody

The antibodies of the current invention bind to a human CD40 antigen on the surface of a human B cell and do not stimulate the growth or differentiation of the B cell. These antibodies may be polyclonal antibodies, monoclonal antibodies, humanize antibodies, single-chain antibodies, and fragments thereof.

1. Antibody Preparation

Monoclonal antibodies 5D12, 3A8 and 3C6 are prepared as described in Example 1 herein. Other monoclonal antibodies of the invention may be prepared similarly, or as follows. First, polyclonal antibodies are raised against the CD40 antigen. Second, monoclonal antibodies specific for CD40 are selected.

a) Polyclonal Sera

Polyclonal sera may be prepared by conventional methods. In general, a solution containing the CD40 antigen is first used to immunize a suitable animal, preferably a mouse, rat, rabbit or goat. Rabbits and goats are preferred for the preparation of polyclonal sera due to the volume of serum obtainable, and the availability of labeled anti-rabbit and anti-goat antibodies. Immunization is generally performed by mixing or emulsifying the antigen-conttig solution in saline, preferably in an adjuvant such as Freund's complete adjuvant, and injecting the mixture or emulsion parenteally (generally subcutaneously or intramuscularly). A dose of 50–200 µg/injection is typically sufficient. Immuniztion is generally boosted 2–6 weeks later with one or more injections of the protein in saline, preferably using Freund's incomplete adjuvant. One may alternatively generate antibodies by in vitro immunization using methods known in the art, which for the purposes of this invention is considered equivalent to in vivo immunization.

Polyclonal antisera are obtained by bleeding the immunized animal into a glass or plastic container, incubating the blood at 25° C. for one hour, followed by incubating at 4° C. for 2–18 hours. The serum is recovered by centrifugation (e.g., 1,000×g for 10 minutes). About 20–50 ml per bleed may be obtained from rabbits.

b) Monoclonal Antibodies

Monoclonal antibodies are prepared using the method of Kohler and Milstein, *Nature* (1975) 256:495–96, or a modification thereof. Typically, a mouse or rat is immunized as described above. However, rather than bleeding the animal to extract serum, the spleen (and optionally several large lymph nodes) are removed and dissociated into single cells. If desired, the spleen cells may be screened (after removal of nonspecifically adherent cells) by applying a cell suspension to a plate or well coated with the protein antigen. B-cells expressing membrane-bound immunoglobulin specific for the antigen bind to the plate, and are not rinsed away with the rest of the suspension. Resulting B-cells, or all dissociated spleen cells, are then induced to fuse with myeloma cells to form hybridomas, and are cultured in a selective medium (e.g., hypoxanthine, aminopterin, thymidine medium, "HAT"). The resulting hybridomas are plated by limiting dilution, and are assayed for the production of antibodies which bind specifically to the desired immunizing cell-surface antigen (and which do not bind to unrelated antigens). The selected mAb-secreting hybridomas are then cultured either in vitro (e.g., in tissue culture bottles or hollow fiber reactors), or in vivo (as ascites in mice).

If desired, the antibodies (whether polyclonal or monoclonal) may be labeled using conventional techniques. Suitable labels include fluorophores, chromophores, radioactive atoms (particularly $^{32}P$ and $^{125}I$), electron-dense reagents, enzymes, and ligands having specific binding partners. Enzymes are typically detected by their activity. For example, horseradish peroxidase is usually detected by its ability to convert 3,3',5,5'-tetramethylbenzidine (TMB) to a blue pigment, quantifiable with a spectrophotometer. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. It should be understood that the above description is not meant to categorize the various labels into distinct classes, as the same label may serve in several different modes. For example, $^{125}I$ may serve as a radioactive label or as an electron-dense reagent. HRP may serve as enzyme or as antigen for a mAb. Further, one may combine various labels for desired effect. For examnple, mAbs and avidin also require labels in the practice of this invention: thus, one might label a mAb with biotin, and detect its presence with avidin labeled with $^{125}I$, or with an anti-biotin mAb labeled with HRP. Other permutations and possibilities will be readily apparent to those of ordinary skill in the art, and are considered as equivalents within the scope of the instant invention.

CD40 Antigen Epitopes

The CD40 antigen epitopes of this invention are molecules that are immunorccctive with anti-CD40 monoclonal antibodies whose binding to a human CD40 antigen located on the surface of a human B cell prevents the growth or differentiation of the B cell. That is, such epitopes compete with the binding of said antibodies to the CD40 antigen. Systematic techniques for identifying these epitopes are known in the art, as described by H. M. Geysen in U.S. Pat. No. 4,708,871, which is incorpod herein by reference. Typically these epitopes are short amino acid sequences. These sequences may be embedded in the sequence of longer peptides or proteins, as long as they are accessible.

The epitopes of the invention may be prepared by standard peptide synthesis techniques, such as solid-phase synthesis. Alternatively, the sequences of the invention may be incorporated into larger peptides or proteins by recombinant methods. This is most easily accomplished by preparing a DNA cassette which encodes the sequence of interest, and ligating the cassette into DNA encoding the protein to be modified at the appropriate site. The sequence DNA may be synthesized by standard synthetic techniques, or may be excised from the phage pIII gene using the appropriate restriction enzymes.

Epitopes identified herein may be prepared by simple solid-phase techniques. The minimum binding sequence may be determined systematically for each epitope by standard methods, for example, employing the method described by H. M. Geysen, U.S. Pat. No. 4,708,871. Briefly, one may synthesize a set of overlapping oligopeptides derived from the CD40 antigen bound to a solid phase array of pins, with a unique oligopeptide on each pin. The pins are araanged to match the format of a 96-well micmoiter plate, permitting one to assay all pins simultaneously, e.g., for binding to an anti-CD40 monoclonal antibody. Using this method, one may readily determine the binding affinity for every possible subset of consecutive amino acids.

Analogs of the invention are also prepared by standard solid-phase methods, and those methods described in PCT application US91/04282.

Formulations and Methods of Administration

The antibodies of this invention are administered at a concentration that is therapeutically effective to prevent or treat antibody-mediated diseases such as allergies, SLE, PBC and ITP. To accomplish this goal, the antibodies may be formulated using a variety of acceptable excipients known in the art. Typically, the antibodies are administered by injection, either intravenously or intraperitoneally. Methods to accomplish this administration are known to those of ordinary skill in the art. It may also be possible to obtain compositions which may be topically or orally administered, or which may be capable of transmission across mucous membranes.

Before administration to patients, formulants may be added to the antibodies. A liquid formulation is preferred. For example, these formulants may include oils, polymers, vitamins, carbohydrates, amino acids, salts, buffers, albumin, surfactants, or bulking agents. Preferably carbohydrates include sugar or sugar alcohols such as mono, di, or polysaccharides, or water soluble glucans. The saccharides or glucans can include fructose, dextrose, lactose, glucose, mannose, sorbose, xylose, maltose, sucrose, dextran, pullulan, dextrin, alpha and beta cyclodextrin, soluble starch, hydroxethyl starch and carboxymethylcellulose, or mixtures thereof. Sucrose is most preferred. "Sugar alcohol" is defined as a $C_4$ to $C_8$ hydrocarbon having an —OH group and includes galactitol, inositol, mannitol, xylitol, sorbitol, glycerol, and arabitol. Mannitol is most preferred. These sugars or sugar alcohols mentioned above may be used individually or in combination. There is no fixed limit to amount used as long as the sugar or sugar alcohol is soluble in the aqueous preparation. Preferably, the sugar or sugar alcohol concentration is between 1.0 w/v % and 7.0 w/v %, more preferable between 2.0 and 6.0 w/v %. Preferably amino acids include levorotary (L) forms of carnitine, arginine, and betaine; however, other amino acids may be added. Preferred polymers include polyvinylpyrrolidone (PVP) with an average molecular weight between 2,000 and 3,000, or polyethylene glycol (PEG) with an average molecular weight between 3,000 and 5,000. It is also preferred to use a buffer in the composition to minimize pH changes in the solution before lyophilization or after reconstitution. Most any physiological buffer may be used, but citrate, phosphate, succinate, and glutamate buffers or mixtures thereof are preferred. Most preferred is a citrate buffer. Preferably, the concentration is from 0.01 to 0.3 molar. Surfactants that can be added to the formulation are shown in EP Nos. 270,799 and 268,110.

Additionally, antibodies can be chemically modified by covalent conjugation to a polymer to increase their circulating half-life, for example. Preferred polymers, and methods to attach them to peptides, are shown in U.S. Pat. Nos. 4,766,106; 4,179,337; 4,495,285; and 4,609,546 which are all hereby incorporated by reference in their entireties. Preferred polymers are polyoxyethylated polyols and polyethylene glycol (PEG). PEG is soluble in water at room temperature and has the general formula: $R(O—CH_2—CH_2)_nO—R$ where R can be hydrogen, or a protective group such as an alkyl or alkanol group. Preferably, the protective group has between 1 and 8 carbons, more preferably it is methyl. The symbol n is a positive integer, preferably between 1 and 1,000, more preferably between 2 and 500. The PEG has a preferred average molecular weight between 1000 and 40,000, more preferably between 2000 and 20,000, most preferably between 3,000 and 12,000. Preferably, PEG has at least one hydroxy group, more preferably it is a terminal hydroxy group. It is this hydroxy group which is preferably activated to react with a free amino group on the inhibitor. However, it will be understood that the type and amount of the reactive groups may be varied to achieve a covalently conjugated PEG/antibody of the present invention.

Water soluble polyoxyethylated polyols are also useful in the present invention. They include polyoxyethylated sorbitol, polyoxyethylated glucose, polyoxyethylated glycerol (POG), etc. POG is preferred. One reason is because the glycerol backbone of polyoxyethylated glycerol is the same backbone occurring naturally in, for example, animals and humans in mono-, di-, triglycerides. Therefore, this branching would not necessarily be seen as a foreign agent in the body. The POG has a preferred molecular weight in the same range as PEG. The structure for POG is shown in Knauf et al., 1988, *J. Bio. Chem.* 263:15064–15070, and a discussion of POG/IL-2 conjugates is found in U.S. Pat. No. 4,766,106, both of which are hereby incorporated by reference in their entireties.

Another drug delivery system for increasing circulatory half-life is the liposome. Methods of preparing liposome delivery systems are discussed in Gabizon et al., *Cancer Research* (1982) 42:4734; Cafiso, *Biochem Biophys Acta* (1981) 649:129; and Szoka, *Ann Rev Biophys Eng* (1980) 9:467. Other drug delivery systems are known in the art and are described in , e.g., Poznansky et al., DRUG DELIVERY SYSTEMS (R. L. Juliano, ed., Oxford, N.Y. 1980), pp. 253–315; M. L. Poznansky, *Pharm Revs* (1984) 36:277.

After the liquid pharmaceutical composition is prepared, it is preferably lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is preferably administered to subjects using those methods that are known to those skilled in the art.

As stated above, the antibodies and compositions of this invention are used to treat human patients to prevent or treat antibody-mediated diseases such as allergies, SLE, PBC and ITP. The preferred route of administration is parenteraly. In parenteral administration, the compositions of this invention will be formulated in a unit dosage injectable form such as a solution, suspension or emulsion, in association with a pharmaceutically acceptable parenteral vehicle. Such vehicles are inherently nontoxic and nontherapeutic. Examples of such vehicles are saline, Ringer's solution, dextrose solution, and Hanks' solution. Nonaqueous vehicles such as fixed oils and ethyl oleate may also be used. A preferred vehicle is 5% dextrose in saline. The vehicle may contain minor amounts of additives such as substances that enhance isotonicity and chemical stability, including buffers and preservatives.

The dosage and mode of administration will depend on the individual. Generally, the compositions are administered so that antibodies are given at a dose between 1 µg/kg and 20 mg/kg, more preferably between 20 µg/kg and 10 mg/kg, most preferably between 1 and 7 mg/kg. Preferably, it is given as a bolus dose, to increase circulating levels by 10–20 fold and for 4–6 hours after the bolus dose. Continuous infusion may also be used after the bolus dose. If so, the antibodies may be infused at a dose between 5 and 20 µg/kg/minute, more preferably between 7 and 15 µg/kg/minute.

The present invention will now be illustrated by reference to the following examples which set forth particularly advantageous embodiments. However, it should be noted that these embodiments are illustrative and are not to be construed as restricting the invention in any way.

EXAMPLES

Materials and Methods

Cell Lines

The mutant mouse thymoma EL-4 subclone EL4B5 was a gift of Dr. R. H. Zubler, Hôpital Cantonal Universitaire, Geneva. Mouse 3T6 transfectant cells expressing hybrid molecules of the HR (high responder) allelic form of human FcγRIIa were a gift of Dr. P. A. M. Warmerdam, Department of Experimental Immunology, University Hospital Utrecht, Utrecht, The Netherlands. Warmerdam et al., *J. Immunol.* (1991) 147:1338. Both cell lines were cultured in Iscove's Modified Dulbecco's Medium (IMDM), supplemented with gentamycin (80 µg/ml) and 10% heat-inactivated fetal calf serum (FCS) (Hyclone, Logan, Utah). To avoid possible loss of B cell activating capacity, every 4 to 8 weeks a new batch of EL4B5 cells was thawed. The cell lines were periodically tested for mycoplasma contamination by the use of a $^3$H-labelled DNA probe for mycoplasma ribosomal RNA (GenProbe, San Diego, Calif.) and were free of mycoplasma during the course of the experiments.

Antibodies and hCD40.Hµ Fusion Protein

Anti-CD40 mAb 5D12, 3C6 and 3A8 were generated by immunizing mice with insect cells expressing recombinant human CD40 as shown in Example 1. Anti-(B7) mAb B7–24 was generated in a similar way by immunizing with insect cells expressing recombinant human B7. Anti-CD40 mAb S2C6 was a gift of Dr. S. Paulie (University of Stockholm, Sweden). Paulie et al., *J. Immunol.* (1989) 142:590. Anti-CD40 mAb G28.5 was donated by Dr. J. A. Ledbetter (Oncogen Corporation, Seattle, Wash., USA). Clark et al., *PNAS (USA)* (1986) 83:4494. Control antibodies were: anti-(β-glucocerebrosidase) mAb 8E4 (IgG1), Barneveld et al., *Eur. J. Biochem.* (1983) 134:585, and myeloma immunoglobulins MOPC-21 (IgG1) and MOPC-141 (IgG2b) (Sigma, St. Louis, Mo.). All mAb were used as purified antibody preparations. hCD40.Hµ fusion protein was a gift of Dr. P. Lane (Basel Institute for Immunology, Basel, Switzerland) and was used as a 5× concentrated supernatant of transfected J558L cells. Lane et al., *Eur. J. Immunol.* (1992) 22:2573.

Human B Lymphocytes

B lymphocytes were isolated from tonsils obtained from children undergoing tonsillectomies, essentially as described in De Groot et al., Lymphokine Research (1990) 9:321. Briefly, the tissue was dispersed with scalpel blades, phagocytic and NK cells were depleted by treatment with 5 mM L-leucine methyl ester and T cells were removed by one cycle of resetting with sheep erythrocytes (SRBC) treated with 2-aminoethyl isothiouronium bromide. The purity of the resulting B lymphocyte preparations was checked by indirect immunofluorescent labelling with anti-(CD20) mAb B1 (Coulter Clone, Hialeah, FA) or anti-(CD3) mAb OKT3 (Ortho, Raritan, N.J.) and a FITC-conjugated F(ab')$_2$ fragment of rabbit anti-(mouse Ig) (Zymed, San Francisco, Calif.), and FACS analysis. The B cell preparations contained (mean±SD of 6 isolations): 95±4% CD20-positive cells and 2±1% CD3-positive cells.

B-Cell Proliferation Assay

B cells ($4\times10^4$ per well) were cultured in 200 µl IMDM supplemented with 10% fetal calf serum in flat bottom 96-well microtiter plates. B cells were stimulated by addition of immobilized anti-(IgM) antibodies (Immunobeads; 5 µg/ml; BioRad, Richmond, Calif.). Where indicated 100 U/ml recombinant IL-2 was added. Varying concentrations of mAbs were added at the onset of the microcultures and proliferation was assessed at day 3 by measurement of the incorporation of [$^3$H]-thymidine after 18 hour pulsing.

Banchereau-Like B-Cell Proliferation Assay

For testing the ability of anti-CD40 mAbs to stimulate B-cell proliferation in a culture system analogous to that described by Banchereau et al., *Science* (1991) 251:70, mouse 3T6 transfectant cells expressing the HR allelic form of human FcγRII were used. B cells ($2\times10^4$ per well) were cultured in flat-bottom microwells in the presence of $1\times10^4$ transfectant cells (irradiated with 5000 Rad) in 200 µl IMDM supplemented with 10% fetal calf serum and 100 U/ml recombinant IL-4. Before addition of the B cells, the 3T6 cells were allowed to adhere to the culture plastic for at least 5 hours. Anti-CD40 mAbs were added at concentrations varying from 15 ng/ml to 2000 ng/ml and proliferation of B cells was assessed by measurement of thymidine incorporation at day 7, upon 18 hour pulsing with [$^3$H]-thymidine.

B-Cell Activation Assay with EL4B5 Cells

B cells (1000 per well) were cultured together with irradiated (5000 Rad) EL4B5 cells ($5\times10^4$ per well) in flat bottom microtiter plates in 200 µl IMDM supplemented with 10% heat-inactivated fetal calf serum, 5 ng/ml phorbol-12-myristate 13-acetate (Sigma) and 5% human T-cell supernatant. MAbs were added at varying concentrations at the onset of the cultures and thymidine incorporation was assessed at day 6 after 18 hour pulsing with [$^3$H]-thymidine. For the preparation of T-cell supernatant, purified T cells were cultured at a density of $10^6$/ml for 36 hours in the presence of 1 µg/ml PHA and 10 ng/ml PMA. Wen et al., supra. T-cell supernatant was obtained by centrifugation of the cells and stored at –20° C. The effectiveness of T-cell supernatants in enhancing proliferation of human B cells in EL4B5-B cell cultures was tested and the most effective supernatants were pooled and used in the experiments.

Human T Cell Helper Assay for Antibody Production by B Cells 96-well tissue culture plates were coated with a 1:500 dilution of ascites fluid of anti-CD3 mAb CLB-T3/3 (CLB, Amsterdam, The Netherlands). As indicated costimulatory mAbs were added: anti CD2 mAbs CLB-T11.1/1 and CLB-T11.2/1 (CLB, Amsterdam, The Netherlands), both ascites 1:1000 and anti-CD28 mAb CLB-28/1 (CLB, Amsterdam, The Netherlands). Subsequently, tonsillar T cells (irradiated, 3000 Rad; $10^5$ per well), tonsillar B cells ($10^4$ per well) and rIL-2 (20 U/ml) were added. The final volume of each cell culture was 200 µl. After 8 days, cells were spun down, and cell-free supernatant was harvested. The concentrations of human IgM and IgG in (diluted) samples were estimated by ELISA as described below.

ELISA Assay for Immunoglobulin Quantification

The concentrations of human IgM and IgG were estimated by ELISA. 96-well ELISA plates were coated with 4 µg/ml mouse anti-human IgG mAb MH 16-01 (CLB, Amsterdam, The Netherlands) or with 1.2 µg/ml mouse anti-human IgM mAb 4102 (Tago, Burlingame, Calif.) in 0.05 M carbonate buffer (pH=9.6), by incubation for 16 h at 4° C. Plates were washed 3 times with PBS-0.05% Tween-20 (PBS-Tween) and saturated with BSA for 1 hour. After 2 washes the plates were incubated for 1 h at 37° C. with different dilutions of the test samples. After 3 washes, bound Ig was detected by incubation for 1 h at 37° C. with 1 µg/ml peroxidase-labeled mouse anti-human IgG mAb MH 16-01 (CLB) or mouse anti-human IgM mAb MH 15-01 (CLB). Plates were washed 4 times and bound peroxidase activity was revealed by the addition of O-phenylenediamine as a substrate. Human standard serum (H00, CLB) was used to establish a standard curve for each assay.

Flow Cytofluorometric Assay

ARC cells ($10^6$ cells/sample) were incubated in 100 µl primary antibody (10 µg/ml in PBS-BSA or Hankis' balanced salt solution (HBSS) supplemented with 1% BSA and 0.05% sodium azide) for 20 min at 4° C. After 3 washes with PBS-BSA or HBSS-BSA, the cells were incubated in 100 µl FITC-labeled F(ab')$_2$ fragments of goat anti-(mouse IgG) antibodies (Jackson, West Grove, Pa.) for 20 min at 4° C. After 3 washes with PBS-BSA or HBSS-BSA and 1 wash with PBS, the cells were resuspended in 0.5 ml PBS. Analyses were performed with a FACSCAN V (Becton Dickinson, San Jose, Calif.).

Alternatively, EL4B5 cells were harvested before and at different time points during culture in medium containing PMA (5ng/ml) and human T-cell supernatant (5%). Cells were incubated for 30 minutes with 10 µl supernatant of transfected cells contning hCD40-Hµ diluted in 100 µl Hank's Balanced Salt Solution supplemented with 0.05% sodium azide (4° C.). This was followed by incubation with FITC-conjugated F(ab')$_2$ fragments of rabbit anti-(human IgM) (Central Laboratory of the Blood Transfusion Service, Amsterdam, The Netherlands). As a control, cells were incubated with the FIT-conjugate only. For analysis a FACScan-4 cytofluorometer (Becton and Dickinson) was used. Non-vital cells were excluded from analysis by the use of propidium iodide.

Example 1

Making Monoclonal Antibodies to B7 and CD40

A. PCR Cloning of CD40 and B7

RNA was isolated from a population of EBV-tmnsformed human spleen cells essentially as described by Chirgwin et al., Biochemistry (1979) 17:5294. In brief, the cells were washed twice with phosphate buffered saline (PBS) and lysed in 5 M guanidinium thiocyanate in the presence of 0.7 M 2-mercaptoethanol. The cell lysate was layered on a discontinuous CsCl gradient (Chirgwin et al.) and centrifuged for 16 hours at 26,000 rpm in a Beckman SW28 rotor. The RNA was recovered by dissolving the pellet in DEPC-treated $H_2O$. The RNA was precipitated with ethanol once, resuspended in DEPC-treated $H_2O$, and stored at −70° C.

Total RNA (10 µg/reaction) was converted to cDNA using random hexamer priming in 50 µl reaction buffer containing 500 units MLV-RT (Bethesda Research Laboratories, Bethesda, Md.), 5 µM random hexamer (Pharmacia, Piscataway, N.J.), 1 mM DTT, dNTP mix (0.5 mM each), 10 mM Tris-HCL pH 8.3, 50 mM KCl, 2.5 mM $MgCl_2$ and 0.1 mg/ml BSA (bovine serum albumin). After incubation at 37° C. for 1 hour, the samples were boiled for 3 minutes and stored at −70° C. The DNA encoding the CD40 and B7 molecules was generated by PCR using primers which contained sequences having homology to known CD40 and B7 sequence, where the primers also encoded restriction sites useful for cloning (FIG. 2). These primers were based on the published cDNA coding sequences for B7 and CD40. Freeman et al., *J. Immunol.* (1989) 143:2714, and Stamenkovic et al., *EMBO J.* (1989) 8:1403. All primers start with a C-G clamp at the 5' end followed by a restriction site for cloning (shown in bold, FIG. 2). The underlined sequences in the backward primers, for the cloning of the soluble forms of B7 and CD40, represents an epitope recognized by a monoclonal antibody used for affinity purification. The numbers in brackets represent the location of the primers relative to the published cDNAs for CD40 and B7.

For PCR amplification, 1 µl of cDNA was mixed with 1 µl (10 picomoles) of a forward primer, 1 µl (10 picomoles) of a backward primer, and 47 µl of PCR mix. The PCR mix consisted of 1.25 units Taq polymerase (Perkin-Elmer/Cetus, Norwalk, Conn.), dNTP mix (0.2 mM each), 10 mM Tris-HC 1 pH 8.3, 50 mM KCl, 2.5 mM $MgCl_2$ and 0.1 mg/ml BSA. The 50 µl of PCR mixture was overlaid with 70 µl mineral oil and subjected to 25 cycles of amplification in a Perkin-Elmer/Cetus thermocycler (denaturation at 95° C. for 30 seconds, primer annealing at 55° C. for 30 seconds and extension at 72° C. for 1.5 minutes). PCR products were obtained after 25 amplification cycles.

The amplification products were digested with BglII and KpnI (FIG. 1B) and isolated by size-fractionation. Before expression in baculovirus, the DNA sequence of each fragment was confirmed by sequencing analysis to prevent the introduction of PCR-induced mutations. The baculovirus transfer vector pAcC8 was also digested with BglII and KpnI (FIG. 1B).

The amplified flagments were ligated to the linear pAcC8 vector (ratio of insert to vector was 3:1). The ligation products were transformed into bacterial strain DH5α (Gibco/BRL, Gaithersburg Md.) and recombinant pAcC8 vectors were selected on the basis of ampicillin resistance. Recombinant plasmids were isolated from bacteria clones (Maniatis et al., *Molecular Cloning: A Laboratory Manual,* (Cold Spring Harbor, N.Y.: Cold Spring Harbor Laboratories), 1982; Ausubel et al., *Current Protocols in Molecular Biology* (Media, PA: John Wiley and Sons)) and the presence of the insert of interest verified using polymerase chain reactions (see above). Large scale plasmid preparation was performed by standard procedures (Ausubel et al.; Maniatis et al; Sambrook et al., *Molecular Cloning: A Laboratory Manual,* (Cold Spring Harbor, N.Y.: Cold Spring Harbor Laboratories), 1989).

B. Baculovirus Expression of Human CD40 and B7

Sequences encoding human CD40 and human B7 were recombined into the *Autographa californica* baculovirus (AcNPV) using the transfer vectors pAcCD40 (encoding the full-length CD40 molecule), pAcCD40-ED/Glu (encoding the extracellular domain of CD40), pAcB7 (encoding the full-length B7 molecule) and pCcB7-ED/Glu (encoding the cellular domain of the B7 molecule).

The plasmids were cotransfected with wild-type baculoviral DNA (2–10 pfu) (AcNPV; Summers et al., *A Manual of*

*Methods for Baculovirus Vectors and Insect Cell Culture Procedures,* Texas Agricultural Experimental Station Bulletin No. 1555 (1987)) into Sf9 (*Spodoptera frugiperda*) cells at a density of $10^6$ cells/ml (Summers et al.). Recombinant baculovirus-infected Sf9 cells were identified and clonally purified (Summers et al.).

For cell surface expression of recombinant proteins the cells were harvested after 48 hours of culture.

C. Sf9 Insect Cell ELISA

Sf9 insect cells infected with recombinant virus were cultured for 48 hours in 24-well plates. After removal of the tissue culture medium the plates were incubated for 45 minutes at room temperature (RT) with 0.25 ml of antibody in PBS with 1% BSA (PBS-BSA). After three washed with PBS-BSA, the plates were incubated for 35 minutes at RT with 250 µl of a 1/250 dilution of goat anti-(mouse total Ig) immunoglobulins conjugated to horseradish peroxidase (Zymed, South San Francisco, Calif.) in PBS-BSA. Unbound peroxidase activity was removed by washing five times with PBS-BSA. Bound peroxidase activity was revealed by the addition of an assay mixture prepared by diluting 0.5 ml of 2 mg/ml 3,3',5,5'-tetramethylbenzidine in ethanol to 10 ml with 10 mM sodium acetate, 10 mM EDTA buffer (pH 5.0) and adding 0.03% (v/v) $H_2O_2$. The reaction was stopped after 10 minutes by adding 100 µl of 1 M $H_2SO_4$.

Figure 3:
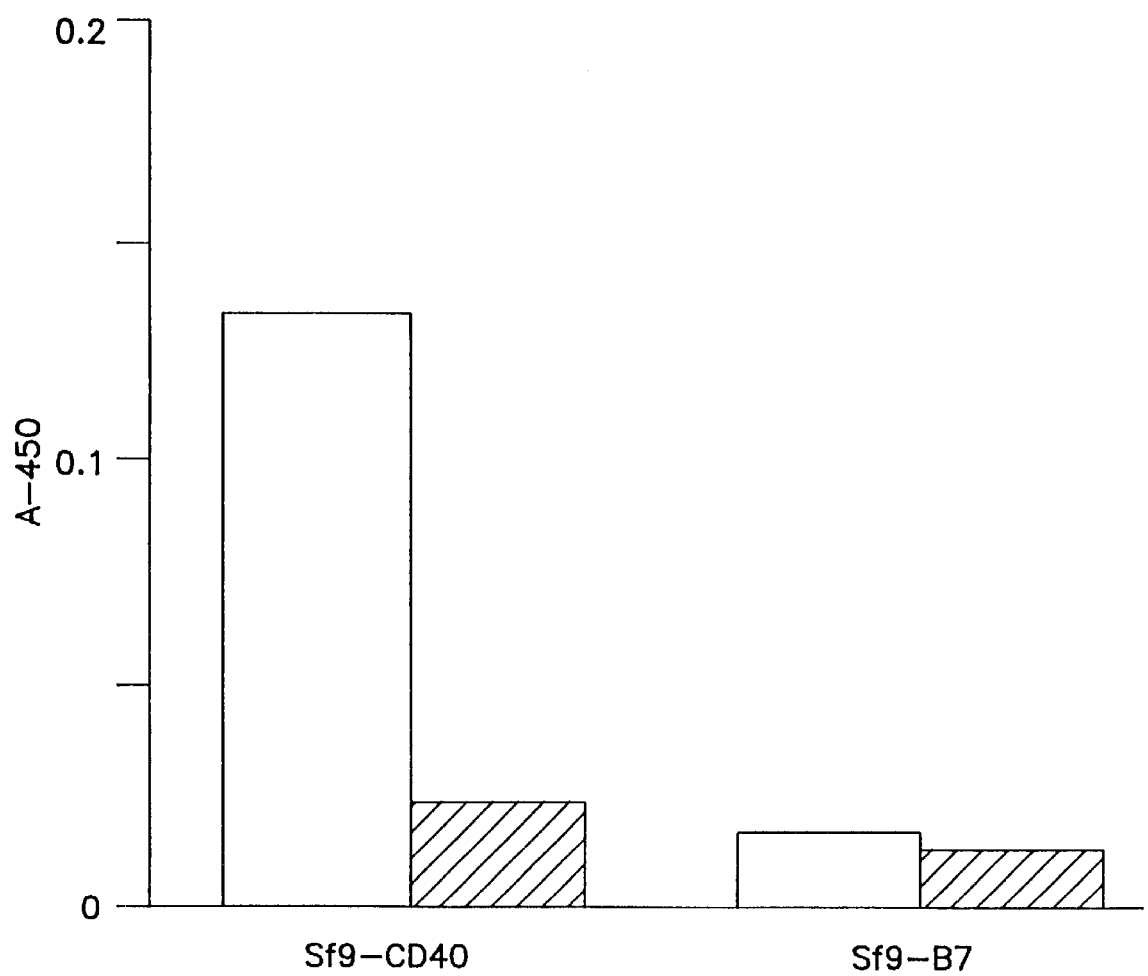
FIG. 3 shows the results of ELISA assays examining the reaction of anti-CD40 monoclonal antibody 52C6 with Sf9 cells expressing CD40 and with Sf9 cells expressing B7.

The above-described ELISA assays performed on live Sf9 cells gave the following results. FIG. 3 presents the data for live Sf9 cells infected with pAcB7 and pAcCD40 which were cultured for 48 hours in 24-well plates. The antibodies used in the ELISA were: S2C6 (anti-CD40, open bars) and no primary antibody (hatched bars).

D. Host Animal Immunization

Female BALB/c mice were injected intraperitoneally at day 0 and day 14 with $5 \times 10^6$ Sf9 cells infected with AcCD40 virus, AcB7 virus or AcCd3 virus (control virus). At day 21, 100 µl of serum was obtained to test for the presence of specific antibodies. After a rest period of at least two weeks, the mice received a final injection with $5 \times 10^6$ cells infected with AcCD40 or AcB7 virus. Three days after this last injection, the spleen cells were used for cell fusion.

E. Generation of Hybridoma Clones

Splenocytes from immunized BALB/c mice were fused with SP2/0 murine myeloma cells at a ratio of 10:1 using 50% polyethylene glycol as previously described by de Boer et al., *J. Immunol. Meth.* (1988) 113:143. The fused cells were resuspended in complete IMDM medium supplemented with hypoxanthine (0.1 mM), aminopterin (0.01 mM), thymidine (0.016 mM) and 0.5 ng/ml hIL-6 (Genzyme, Cambridge, Mass.). The fused cells were then distributed between the wells of 96-well tissue culture plates, so that each well contained 1 growing hybridoma on average.

Figure 4A:
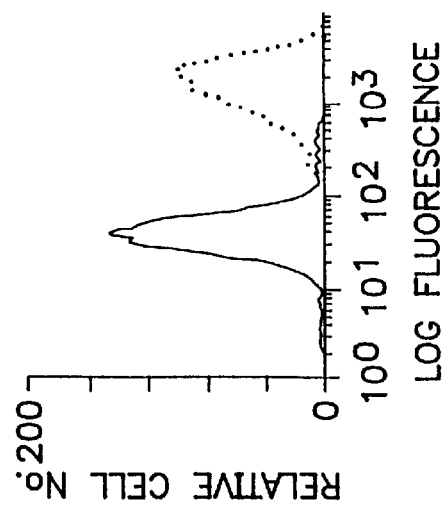
FIGS. 4A–4C shows the results of the fluorescent cell staining of EBV-transformed B-cell line ARC cells expressing CD40.
Figure 4B:
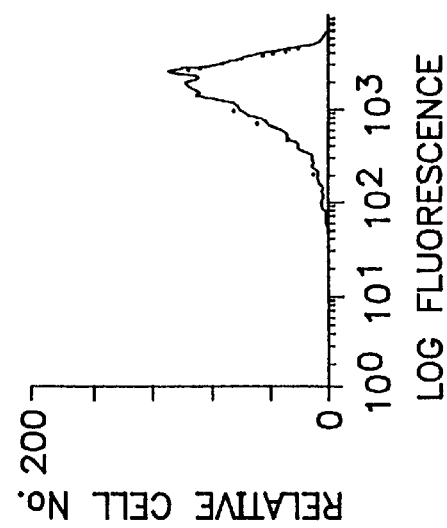
Figure 4C:
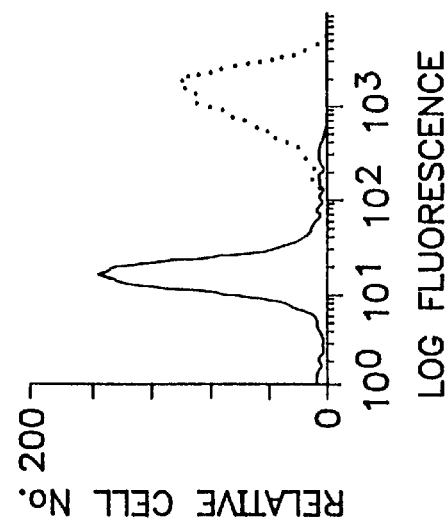

After 10–14 days the supernatants of the hybridoma populations were screened for specific antibody production. For the screening of specific antibody production by the hybridoma clones, the supernatants of 12 wells were pooled and used for fluorescent cell staining of EBV-transformed B cells as described for the FACS Assay above. Subsequently, the supernatants of the positive pools were tested individually. Positive hybridoma cells were cloned three times by limiting dilution in IMDM/FBS containing 0.5 ng/ml hIL-6. Three hybridomas producing anti-CD40 antibodies are labelled 5D12, 3A8 and 3C6. The data is presented in FIG. 4, which shows that a soluble form of CD40, but not of B7 can block the binding of the anti-CD40 mAb 5D12 to CD40 expressing EBV-transformed B cells. FIG. 4 shows fluorescent cell staining of ARC EBV-transformed B cells with 5D12 in the presence and absence of soluble B7 and soluble CD40. 5D12 and the soluble B7, soluble CD40, or controls were preincubated at RT for 20 min before addition to the ARC cells. FIG. 4A shows staing with 5D12 (doted line) or second antibody only (solid line), FIG. 4B shows staining with 5D12 alone (dotted line) or preincubated with soluble B7 (solid line) and, FIG. 4C shows stining with 5D12 alone (dotted line) or preincubated with soluble CD40.

Example 2

Costimulation of B-Cell Proliferation Using Anti-CD40 mAbs

Four hybridomas producing monoclonal antibodies against human CD40 were generated in Example 1. These mAbs were shown to bind to a similar proportion of tonsillar B cells as anti-CD40 mAb G28.5 does. de Boer et al. *J. Immunol. Methods* (1992) 152:15. Three of these monoclonal antibodies (5D12, 3A8 and 3C6) which were of the IgG2b subclass, were tested for their ability to deliver activation signals to human B cells in the B-cell proliferation assay described above.

Figure 5A:
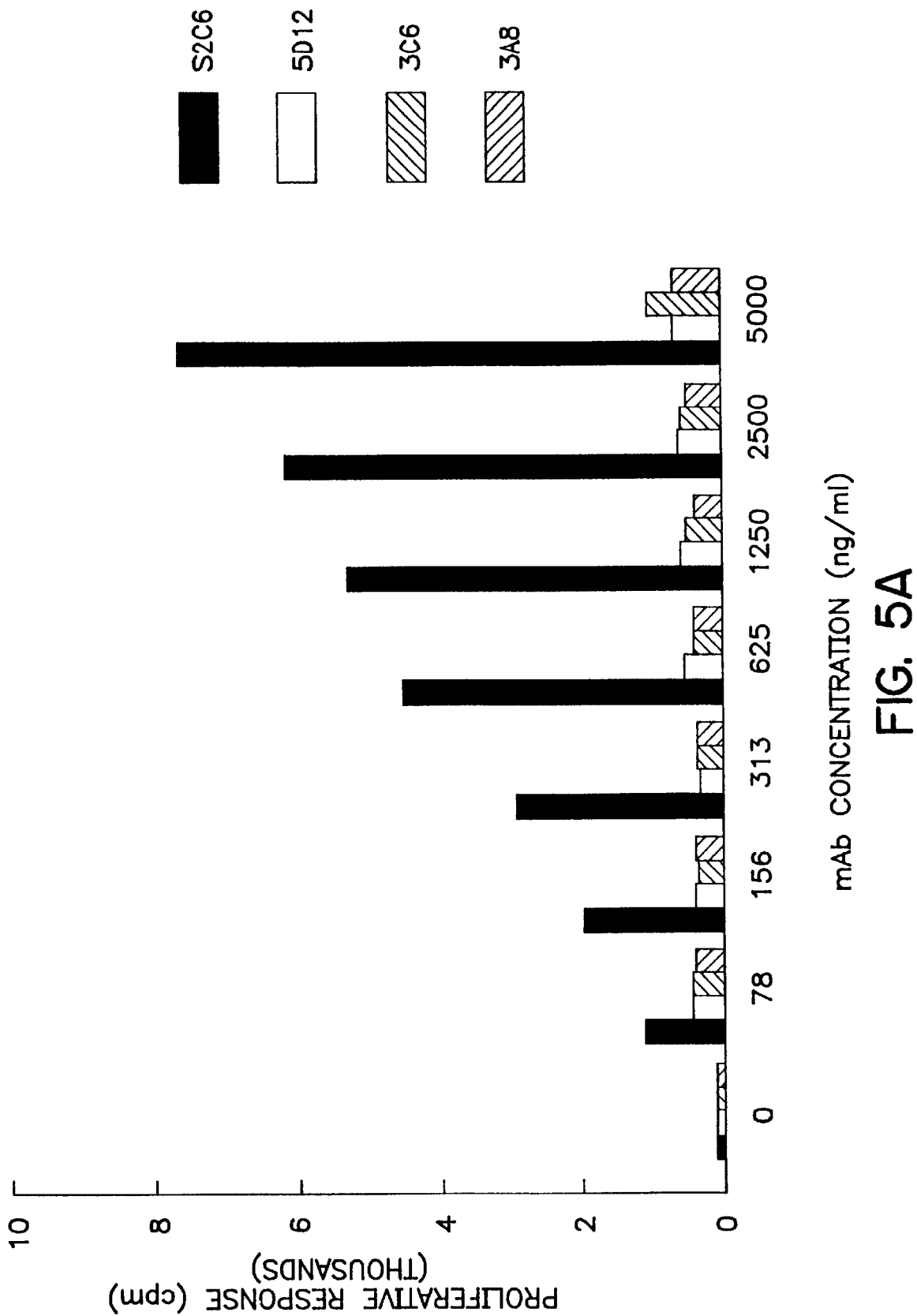
FIG. 5A compares the ability of three new and one old anti-CD40 mAbs to co-stimulate anti-IgM induced human B-cell proliferation.
Figure 5B:
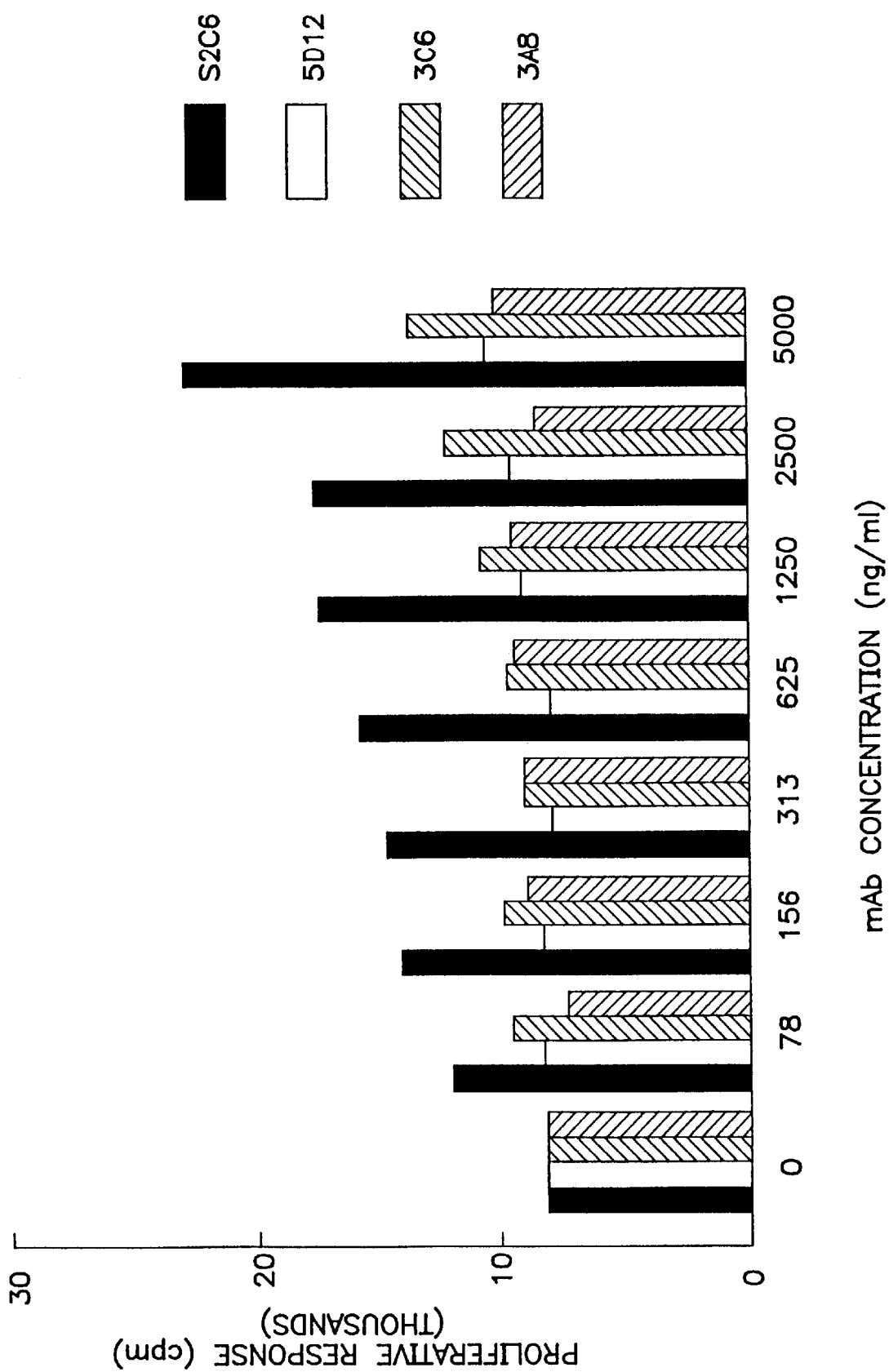
FIG. 5B repeats the experiment of FIG. 5A in the presence of recombinant interleukin-2 (rIL-2).

Human tonsillar B cells ($4 \times 10^4$ per well) were cultured in 200 µl in microwells in the presence of anti-IgM coupled to Sepharose beads (5 µ/ml) (FIG. 5A) or in the presence of anti-IgM plus rIL-2 (100 U/ml) (FIG. 5B). Varying concentrations of the anti-CD40 mAbs S2C6, 5D12, 3C6 or 3A8 were added and [$^3$H]thymidine incorporation was measured at day 3 after 18 h pulsing. Data presented in FIG. 5A are means derived from experiments with B-cell preparations from three different donors with duplicate incubations. Data of FIG. 5B are means of duplicate incubations from one experiment out of two with comparable results.

None of the novel anti-CD40 mAbs was able to significantly costimulate human B-cell proliferation in the presence of immobilized anti-IgM or in the presence of immobilized anti-IgM and IL-2. In contrast, anti-CD40 mAb S2C6 costimulated human B-cell proliferation in a concentration dependent fashion.

Example 3

Induction of B-Cell Proliferation Using Anti-CD40 mAbs

The mAbs tested in Example 2 were tested for their ability to induce proliferation of human B cells in the Banchereau-like Assay described above, i.e., by presenting the anti-CD40 mAb on adherent cells expressing FcγRII. As antibody presenting cells, mouse 3T6 transfectant cells expressing the HR allellic form of human FcγRII were used. It was observed that anti-CD40 mAb S2C6 together with IL-4 induced substantial proliferation of tonsillar human B cells in this system, as assessed by measurement of [$^3$H] thymidine incorporation. Anti-CD40 mabs 5D12, 3C6 or 3A8 however, did not induce proliferation of human B cells in this culture system (data not shown).

Example 4

Inhibition of S2C6 Stimulated B-Cell Proliferation Using Anti-CD40 mAbs

The mAbs were also tested for their ability to inhibit the costimulation of human B-cell proliferation by anti-CD40 mAb S2C6 using the B-cell Proliferation Assay described above. Human tonsillar B cells ($4 \times 10^4$ per well) were cultured in 200 μl in microwells in the presence of anti-IgM coupled to Sepharose beads (5 μg/ml) and anti-CD40 mAb S2C6 (1.25 μg/ml). Varying concentrations of anti-CD40 mAbs 5D12, 3C6 or 3A8 were added and [$^3$H]thymidine incorporation was assessed after 3 days. As a control anti-(glucocerebrosidase) mAb 8E4 was added in similar concentrations. Barneveld et al. *Eur. J. Biochem.* (1983) 134:585. Data are means±S.D. derived from experiments with B cells from two different donors with duplicate incubations.

Figure 6:
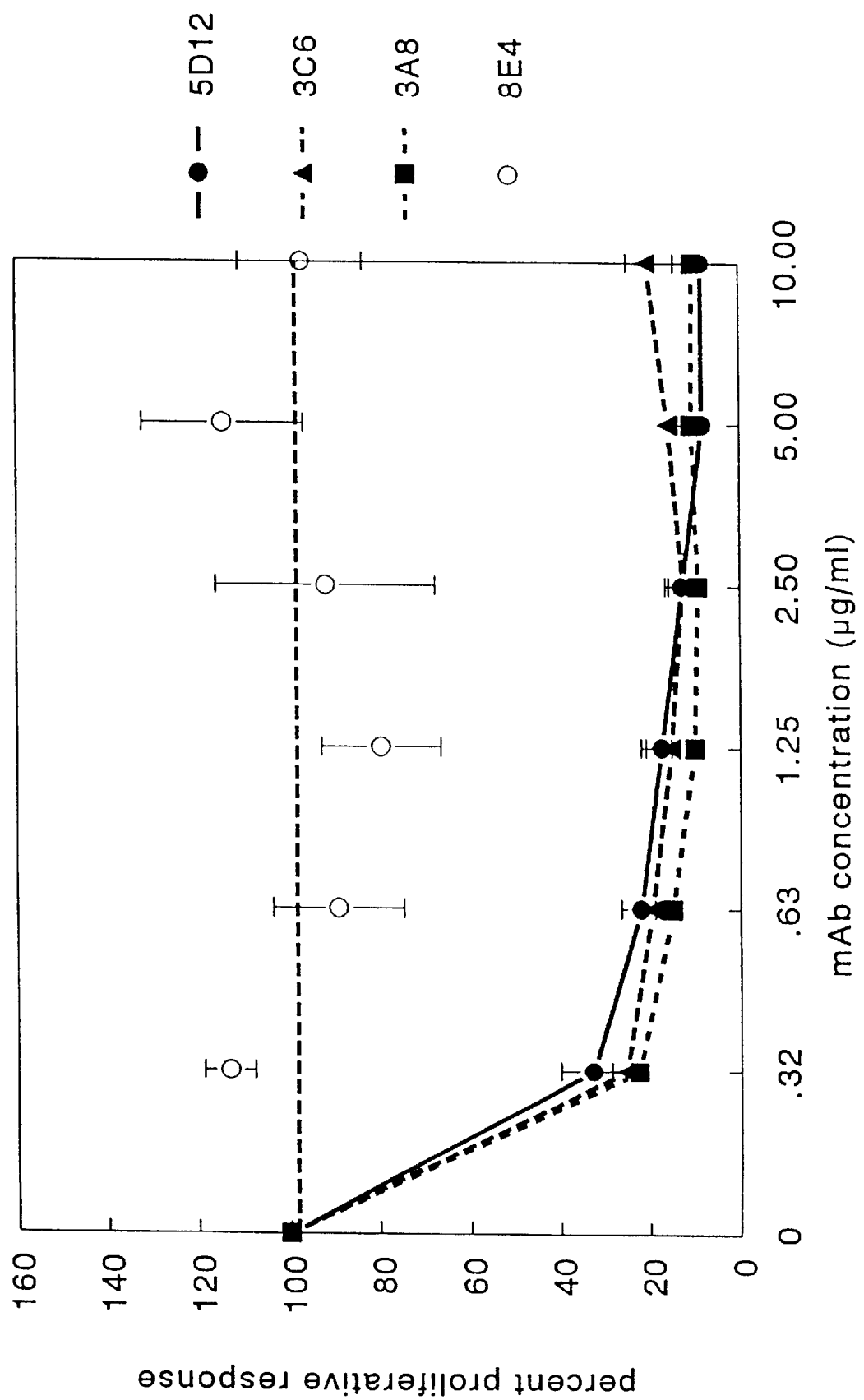
FIG. 6 shows the ability of three new anti-CD40 mAbs to inhibit human B-cell proliferation induced by costimulation with immobilized anti-IgM and anti-CD40 mAb 52C6.

It was found that each of the anti-CD40 mAbs 5D12, 3A8 and 3C6 could inhibit the costimulation of anti-IgM induced human B-cell proliferation by mAb S2C6 (FIG. 6). In contrast, no significant inhibition was seen with equivalent amounts of non-relevant mAb 8E4, directed to β-glucocerebrosidase. Barneveld et al., supra. Thus, it was concluded that these anti-CD40 mAbs do not deliver stimulatory signals to induce the proliferation of human B cells, but, conversely, can inhibit stimulatory signals exerted by triggering CD40 with another mAb. Therefore, these mAbs were considered to be excellent tools to investigate whether signaling via CD40 plays a role in the stimulation of human B-cell proliferation by EL4B5 cells.

Example 5

Effects of Anti-CD40 mAbs on EL4B5-Induced Human B-Cell Proliferation

The effect of anti-CD40 mAbs on EL4B5-induced human B-cell proliferation was tested using the B-cell Activation Assay described above. Human tonsillar B cells (1000 per well) were cultured together with irradiated EL4B5 cells (50,000 per well) in the presence of 5% supernatant of activated human T cells and 5 ng/ml PMA. Anti-CD40 mAbs 5D12, 3C6 or 3A8 were added in varying concentrations. As a control, mAb MOPC-141 (IgG2b) was added. After six days of culture, [$^3$H]thymidine incorporation was assessed.

Figure 7:
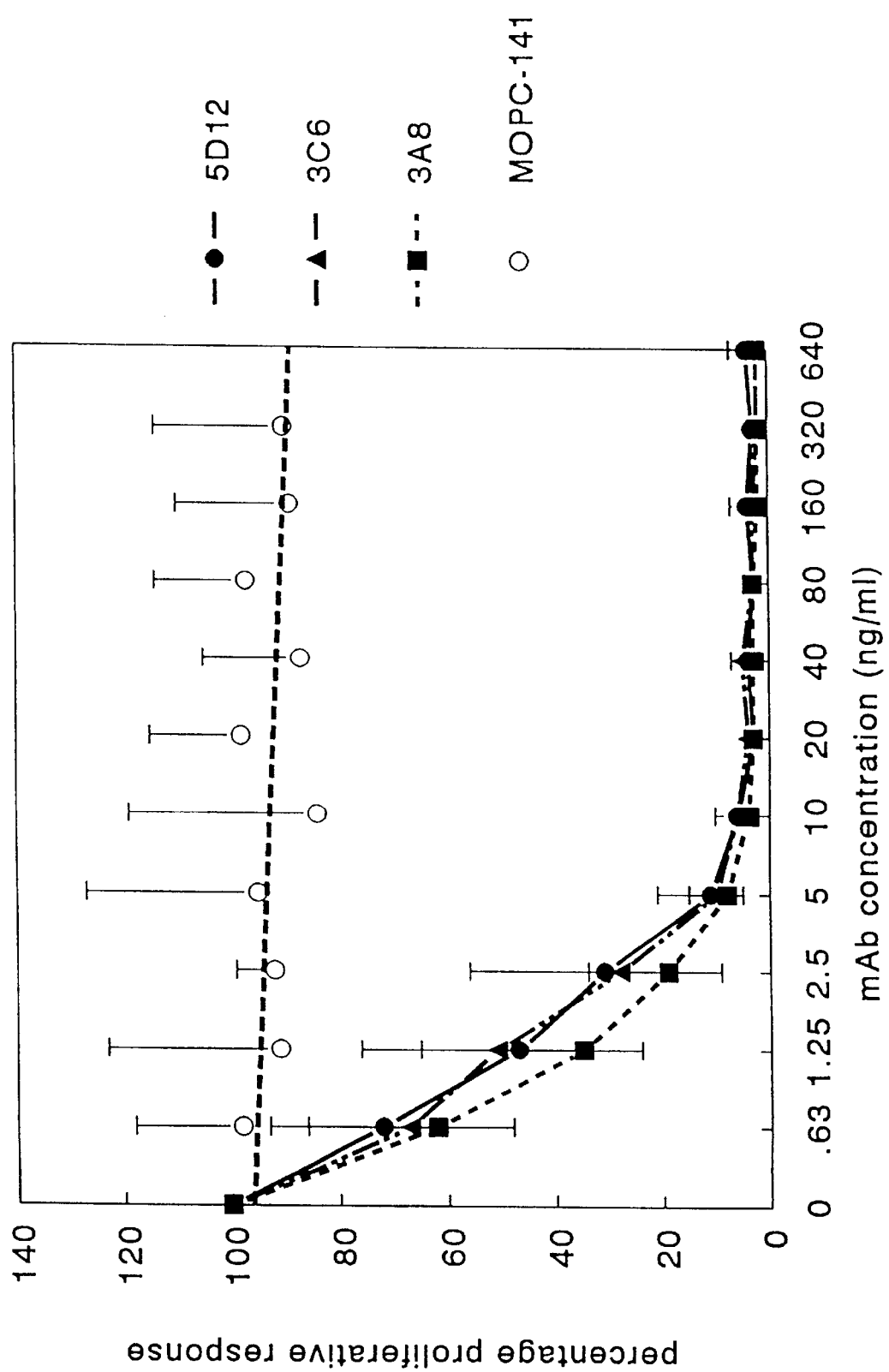
FIG. 7 shows the effect of three new anti-CD40 mAbs on EL4B5-induced human B-cell proliferation.

FIG. 7 shows that addition of anti-CD40 mAbs 5D12, 3C6 or 3A8 resulted in a concentration-dependent inhibition of human B-cell proliferation. Data are means±S.D. derived from experiments with B cells from four different donors with duplicate incubations. [$^3$H]-thymidine incorporation values found for incubations without mAb were (means±S.D.) 10460±1843 cpm, 6982±1729 cpm, 4362±1020 cpm and 1543±3190 in the four different experiments, respectively. [3H]-thymidine incorporation in B cells alone amounted to 40±5 cpm and in irradiated EL4B5 cells alone 31±15 cpm.

Very potent inhibition occurred. At concentrations as low as 10 ng/ml each, the three anti-CD40 mAbs 5D12, 3C6 and 3A8 inhibited human B-cell proliferation completely. Half-maximal inhibition was found at about 1 ng/ml. In contrast, isotype matched IgG2b mouse myeloma protein MOPC-141 had no significant effect on [$^3$H]-thymidine incorporation. Similar inhibition was observed when [$^3$H]-thymidine incorporation was assessed at day 4 of the culture instead of day 6, thus excluding the possibility that the observed effect was due to a change in the kinetics of the proliferation under influence of the anti-CD40 mAb (data not shown).

For comparison, the influence of a few mAb directed against other B-cell surface structures was investigated. Neither anti-CD20 mAb B1 or anti-B7 mAb B7–24 (the latter mAb was generated by a prrcedure similar to that used for generating the anti-CD40 mAb used in FIG. 7, in concentrations similar to those used in the experiments with the anti-CD40 mAb, had any effect on EL4B5-induced human B-cell proliferation (data not shown). Therefore, it may be concluded that the inhibitory effect of anti-CD40 mAb on EL4B5-induced B-cell proliferation is not due to masking of the B-cell surface.

Example 6

Effects of hCD40.Hμ on EL4B5-Induced Human B-Cell Proliferation

Figure 8:
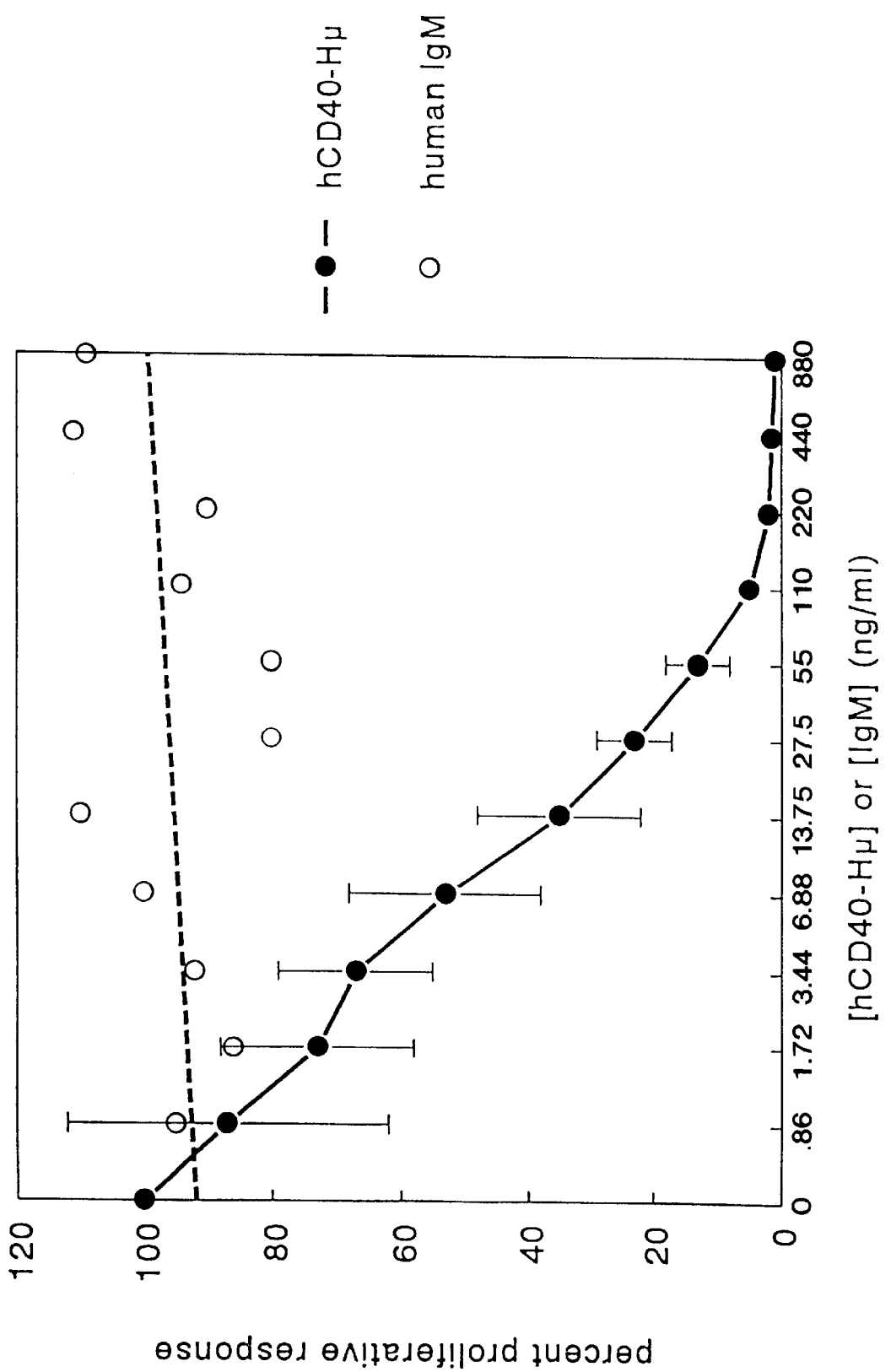
FIG. 8 shows the effect of soluble CD40 (hCD40. $\mu$) on EL4B5-induced human B-cell proliferation.

In order to investigate whether EL4B5 cells expressed a membrane structure which binds CD40, a fusion protein consisting of the extracellular domain of CD40 and human IgM constant domains $CH_2$, $CH_3$ and $CH_4$ (hCD40.Hμ) was used for flow fluorocytometric analysis. Lane et al., supra. Non-activated EL4B5 cells did not bind the fusion protein. However, upon culturing EL4B5 cells together with PMA (5 ng/ml) and 5% human T-cell supernatant, which are the conditions needed for activation of human B cells, a low binding of hCD40.Hμ was found (data not shown). This small shift in fluorescence was found consistently in three independent experiments. The minimal activation period needed for induction of the CD40 binding was 24 hours. To determine whether binding of hCD40.Hμ to the EL4B5 cells would inhibit EL4B5-induced human B-cell proliferation like anti-CD40 mAb did, the fusion protein was titrated into cocultures of EL4B5 cells with human B cells using the B-cell Activation Assay described above. FIG. 8 shows that the fusion protein did indeed inhibit [$^3$H]-thymidine incorporation in a concentration-dependent manner and, like the anti-CD40 mAb used in the experiments shown in FIG. 7, was able to inhibit B-cell proliferation induced by the EL4B5 cells completely.

Example 7

Figure 9A:
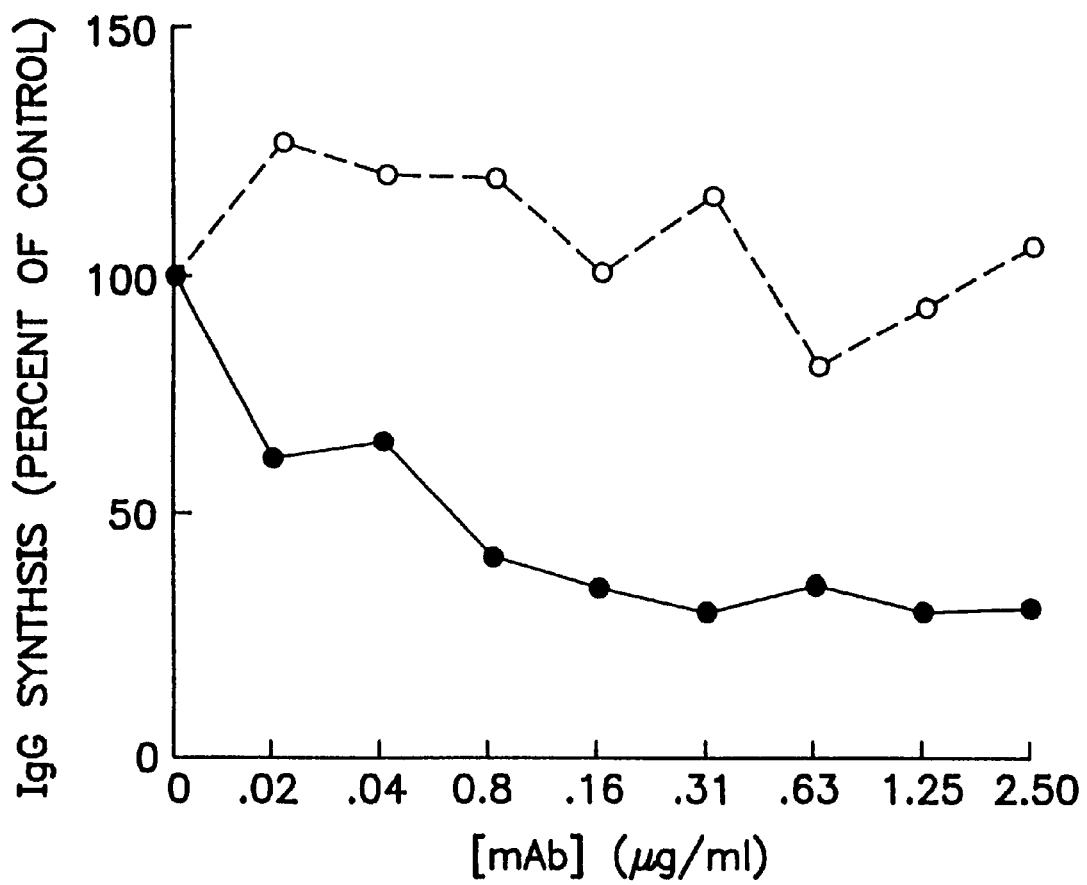
FIGS. 9A and 9B show the effect of one new anti-CD40 mAb 5D12 on human T-cell induced immunoglobulin production by human B cells.

Effects of Anti-CD40 mAbs on Human T-Cell-Induced Antibody Production by Human B-Cells The antibodies were also tested for their capacity to inhibit immunoglobulin production by B cells, stimulated in a contact-dependent manner with activated T cells using the T-cell helper assay described above. Human tonsillar B cells ($10^4$/well) were cultured together with irradiated purified T cells (3000 rad, $10^5$/well) in 96-well plates, coated with anti-CD3 mAb and with or without different mAbs to costimulate the T cells. After 8 days of culture the supernatants were harvested for the determination of immunoglobulin production by the B cells. Immunoglobulin production by the B cells was assessed by the ELISA assay described above. Anti-CD40 mAb 5D12 was added in varying concentrations from the onset of the cultures. As a control, mnAb MOPC-141 was added. FIG. 9A shows that when T cells were stimulated with immobilized anti-CD3 mAb and costimulated with soluble anti-CD2 and anti-CD28 mAbs, addition of anti-CD40 mAb 5D12 resulted in a concentration dependent inhibition of IgG production by human B cells. IgM production by the B cells was inhibited to the same extent. Similar results were obtained with the anti-CD40 mAbs 3C6 and 3A8 and with the hCD40.Hμ fusion protein.

The anti-CD40 mAbs of this invention exhibited very potent inhibition. At concentrations as low as approximately 30 ng/ml, each of the three anti-CD40 mAbs gave 50% of maximal inhibition. In contrast, the isotype-matched IgG2b mouse myeloma protein MOPC-141 had no effect on the immunoglobulin production.

Figure 9B:
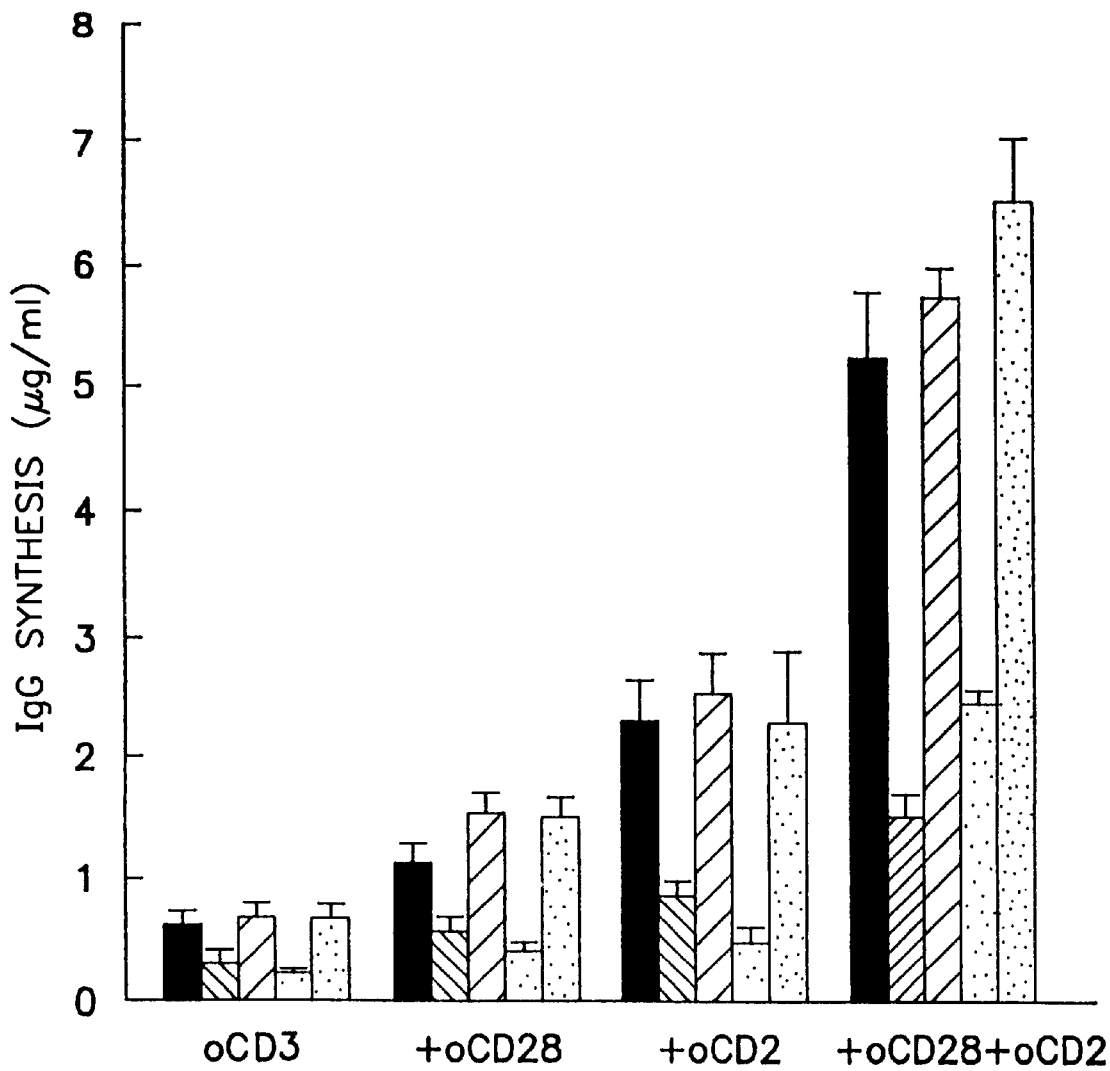

The inhibitory effect by the three anti-CD40 mAbs was not specific for the manner of activation of the T cells providing the CD40 ligand helper activity. FIG. 9B shows that under all the T-cell stimulation conditions (anti-CD3 alone; anti-CD3+anti-CD2; anti-CD3+anti-CD28; and anti-CD3+anti-CD2+anti-CD28), addition of the anti-CD40 mAb 5D12 results in strong inhibition of immunoglobulin production by the human B cells. The inhibition is comparable to the amount of inhibition with the hCD40.Hµ fusion protein, known to completely block the CD40-CD40 ligand interaction. The percentage of inhibition varied from 40 to 70% depending on the T-cell activation conditions. In contrast, the isotype-matched IgG2b mouse myeloma protein MOPC-141, or human IgM (as control for the hCD40.Hµ fusion protein) had no effect on immunoglobulin production by the human B cells.

Deposition of Cultures

The hybridomas used in the above examples, to illustrate the method of the present invention were deposited in and accepted by the American Type Culture Collection (ATCC), 10801 University Boulevard, Manassas, Va. 20110-2209, under the terms of the Budapest Treaty.

| Hybridoma | Deposit Date | Accession No. |
| --- | --- | --- |
| B7-24 | May 6, 1993 | HB 11341 |
| 3C6 | May 6, 1993 | HB 11340 |
| 5D12 | May 6, 1993 | HB 11339 |
| 3A8 | January 30, 1996 | HB 12024 |

The present invention has been described with reference to specific embodiments. However, this application is intended to cover those changes and substitutions which may be made by those skilled in the art without departing from the spirit and the scope of the appended claims.

We claim:

1. A method for treating an antibody-mediated disease in a patient, said antibody-mediated disease being selected from the group consisting of systemic lupus erythemutosis (SLE), primary biliary cirrhosis (PBC), and idiopathic thrombo-cytopenic purpura (ITP), the method comprising administering to a patient in need of such treatment a therapeutically effective amount of an anti-CD40 monoclonal antibody or an antigen binding fragment thereof, said monoclonal antibody or fragment thereof being free of significant agonistic activity and binding to a human CD40 antigen located on the surface of a human B cell, wherein the binding of the antibody to the CD40 antigen on the surface of said B cell prevents the growth or differentiation of the B cell.

2. The method of claim 1 wherein the monoclonal antibody is selected from the group consisting of 5D12, 3A8 and 3C6, which are secreted by a hybridoma having ATCC accession numbers HB 11339, HB 12024 and HB 11340, respectively.

3. The method of claim 2 wherein the monoclonal antibody is 5D12, which is secreted by a hybridoma having ATCC accession numbers HB 11339.

4. The method of claim 2 wherein the monoclonal antibody is 3A8, which is secreted by a hybridoma having ATCC accession numbers HB 12024.

5. The method of claim 2 wherein the monoclonal antibody is 3C6, which is secreted by a hybridoma having ATCC accession numbers HB 11340.

6. The method of claim 1 wherein said antibody-mediated disease is SLE.

7. The method of claim 6 wherein the monoclonal antibody is selected from the group consisting of 5D12, 3A8 and 3C6, which are secreted by a hybridoma having ATCC accession numbers HB 11339, HB 12024 and HB 11340, respectively.

8. The method of claim 7 wherein the monoclonal antibody is 5D12, which is secreted by a hybridoma having ATCC accession numbers HB 11339.

9. The method of claim 7 wherein the monoclonal antibody is 3A8, which is secreted by a hybridoma having ATCC accession numbers HB 12024.

10. The method of claim 7 wherein the monoclonal antibody is 3C6, which is secreted by a hybridoma having ATCC accession numbers HB 11340.

11. The method of claim 1 wherein the antibody-mediated disease is PBC.

12. The method of claim 11 wherein the monoclonal antibody is selected from the group consisting of 5D12, 3A8 and 3C6, which are secreted by a hybridoma having ATCC accession numbers HB 11339, HB 12024 and HB3 11340, respectively.

13. The method of claim 12 wherein the monoclonal antibody is 5D12, which is secreted by a hybridoma having ATCC accession numbers HB 11339.

14. The method of claim 12 wherein the monoclonal antibody is 3A8, which is secreted by a hybridoma having ATCC accession numbers HB 12024.

15. The method of claim 12 wherein the monoclonal antibody is 3C6, which is secreted by a hybridoma having ATCC accession numbers HB 11340.

16. The method of claim 1 wherein the antibody-mediated disease is ITP.

17. The method of claim 16 wherein the monoclonal antibody is selected from the group consisting of 5D12, 3A8 and 3C6, which are secreted by a hybridoma having ATCC accession numbers HB 11339, HB 12024 and HB 11340, respectively.

18. The method of claim 17 wherein the monoclonal antibody is 5D12, which is secreted by a hybridoma having ATCC accession numbers HB 11339.

19. The method of claim 17 wherein the monoclonal antibody is 3A8, which is secreted by a hybridoma having ATCC accession numbers HB 12024.

20. The method of claim 17 wherein the monoclonal antibody is 3C6, which is secreted by a hybridoma having ATCC accession numbers HB 11340.

* * * * *

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
      (A) LENGTH: 50 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 1:

GATCCACCAT GGAGCTCGAG ATCTAGAATT CTGCAGCCCG GGTACCGATC     50

(2) INFORMATION FOR SEQ ID NO: 2:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 2:

GCGCTGCAGC ATCTGAAGCC ATGGGCC     27

(2) INFORMATION FOR SEQ ID NO: 3:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 3:

CGCGGTACCT TGCTTCTGCG GACACTG     27

(2) INFORMATION FOR SEQ ID NO: 4:

(i) SEQUENCE CHARACTERISTICS:
      (A) LENGTH: 61 base pairs

```
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 11..40
        (D) OTHER INFORMATION: /note= "The underlining represents
            an epitope recognized by a monoclonal antibody
            used for affinity purification."

(xi) SEQUENCE DESCRIPTION: SEQ ID NO: 4:

GCGCGGTACC TTACTCCATG GGCATGTATT CCTCTTCCTC GTTATCAGGA AAATGCTGTT      60

G                                                                      61

(2) INFORMATION FOR SEQ ID NO: 5:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

GCGTAGATCT GGTCTCACCT CGCCATGGTT CG                                    32

(2) INFORMATION FOR SEQ ID NO: 6:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

GCGTGGTACC CCACACTCCT GGGTGGGTGC AGCC                                  34

(2) INFORMATION FOR SEQ ID NO: 7:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 11..40
        (D) OTHER INFORMATION: /note= "The underlining represents
            an epitope recognized by a monoclonal antibody
            used for affinity purification."

(xi) SEQUENCE DESCRIPTION: SEQ ID NO: 7:

GCGTGGTACC TTACTCCATG GGCATGTATT CCTCTTCCTC ATCAGTCTTG TTTGTGCCTG      60

C                                                                      61
```